United States Patent
McLane

(10) Patent No.: US 12,235,215 B2
(45) Date of Patent: Feb. 25, 2025

(54) PROCESSING AND IMAGING TISSUE SAMPLES

(71) Applicant: Akoya Biosciences, Inc., Menlo Park, CA (US)

(72) Inventor: Michael McLane, Menlo Park, CA (US)

(73) Assignee: Akoya Biosciences, Inc., Menlo Park, CA (US)

( * ) Notice: Subject to any disclaimer, the term of this patent is extended or adjusted under 35 U.S.C. 154(b) by 661 days.

(21) Appl. No.: 17/380,631

(22) Filed: Jul. 20, 2021

(65) Prior Publication Data

US 2022/0018778 A1 Jan. 20, 2022

Related U.S. Application Data

(60) Provisional application No. 63/054,226, filed on Jul. 20, 2020.

(51) Int. Cl.
  *G01N 21/64* (2006.01)
  *G01N 1/30* (2006.01)
  *G06T 7/00* (2017.01)

(52) U.S. Cl.
  CPC .......... *G01N 21/6456* (2013.01); *G01N 1/30* (2013.01); *G01N 21/6428* (2013.01); *G06T 7/0012* (2013.01); *G01N 2001/302* (2013.01); *G01N 2001/305* (2013.01); *G01N 2021/6441* (2013.01); *G06T 2207/10064* (2013.01); *G06T 2207/30024* (2013.01)

(58) Field of Classification Search
CPC .. G01N 21/6456; G01N 1/30; G01N 21/6428; G01N 2001/302; G01N 2001/305; G01N 2021/6441; G06T 7/0012; G06T 2207/10064; G06T 2207/30024
USPC ........................................................ 382/128
See application file for complete search history.

(56) References Cited

U.S. PATENT DOCUMENTS 7,555,155 B2   6/2009  Levenson et al.
8,330,087 B2  12/2012  Domenicali
(Continued)

FOREIGN PATENT DOCUMENTS

EP   2 601 513   5/2014
EP   3 469 548   5/2020
(Continued)

OTHER PUBLICATIONS

The U.S. Appl. No. 63/171,297, filed Apr. 6, 2021.
(Continued)

*Primary Examiner* — Michael R Neff
(74) *Attorney, Agent, or Firm* — Fish & Richardson P.C.

(57) ABSTRACT

Methods include applying a first stain composition comprising a fluorescent counterstain to a biological sample, measuring information corresponding to one or more stains of the first stain composition, removing the fluorescent counterstain from the biological sample, applying a second stain composition to the biological sample, measuring information corresponding to one or more stains of the second stain composition in the biological sample, where the one or more stains include a fluorescent label, and generating a first image of the biological sample, where the first image corresponds to a pattern of simulated hematoxylin staining in the biological sample.

30 Claims, 23 Drawing Sheets

(56) References Cited

U.S. PATENT DOCUMENTS

| | | | |
|---|---|---|---|
| 8,462,981 B2 | 6/2013 | Determan et al. | |
| 9,541,504 B2 | 1/2017 | Hoyt | |
| 9,909,167 B2 | 3/2018 | Samusik et al. | |
| 10,126,242 B2 | 11/2018 | Miller et al. | |
| 10,370,698 B2* | 8/2019 | Nolan | C12Q 1/6813 |
| 2006/0050946 A1* | 3/2006 | Mitchison | G06T 7/0012 |
| | | | 382/133 |
| 2015/0065371 A1* | 3/2015 | Seppo | G01N 33/57423 |
| | | | 506/9 |
| 2019/0169620 A1* | 6/2019 | Pietilä | C12N 15/1138 |
| 2019/0339203 A1 | 11/2019 | Miller et al. | |

FOREIGN PATENT DOCUMENTS

| | | | | |
|---|---|---|---|---|
| WO | WO 2020/163397 | 8/2020 | | |
| WO | WO 2021/067475 | 4/2021 | | C12Q 1/6804 |
| WO | WO 2021/127637 | 6/2021 | | C12Q 1/682 |

OTHER PUBLICATIONS

The U.S. Appl. No. 63/189,056, filed May 14, 2021.
The International Search Report and Written Opinion of the International Searching Authority for International Application No. PCT/US2021/042353, dated Nov. 3, 2021.

* cited by examiner

PROCESSING AND IMAGING TISSUE SAMPLES

CROSS-REFERENCE TO RELATED APPLICATIONS

This application claims priority to U.S. Provisional Patent Application No. 63/054,226, filed on Jul. 20, 2020, the entire contents of which are incorporated by reference herein.

TECHNICAL FIELD

This disclosure relates to assessment of tissue samples for pathology and other applications.

BACKGROUND

For pathology assessment of tissue samples, conventional methods often involve staining a first tissue section cut from a sample (e.g., a tissue block) with one or more immunohistochemical reagents, and staining a second tissue section cut from the same sample with a combination of hematoxylin and eosin (H&E) stains. An H&E image of the second tissue section can provide morphological and other information to a pathologist that is useful for interpretation of an image of the immunohistochemical reagents in the first tissue section.

SUMMARY

The methods, systems, reagents, and kits described herein can be used to provide a simulated hematoxylin and eosin view of a tissue sample, without applying both hematoxylin and eosin to the tissue sample. In particular, the workflows described herein can use reagents such as curcumin and/or carmine to stain a tissue sample. An image of a tissue sample stained with these reagents can be used to approximate the localization and appearance of hematoxylin in the tissue sample. The workflows described herein can also or alternatively use reagents such as eosin and/or indigo carmine to stain the tissue sample. An image of the tissue sample stained with these reagents reveals or approximates the localization and appearance of eosin in the tissue sample. The two images can then be combined computationally to yield a simulated H&E image of the tissue sample. The simulated image can be used for pathology assessment of the tissue sample, including determining whether to proceed with further staining and imaging steps, and interpreting the observed localization of further stains (e.g., immunohistochemical stains, fluorescent labels) in the tissue sample.

In general, in an aspect, the disclosure features methods that include: applying a first stain composition to a biological sample, and measuring information corresponding to one or more stains of the first stain composition in the biological sample, where the one or more stains comprise a fluorescent counterstain; removing the fluorescent counterstain from the biological sample; applying a second stain composition to the biological sample, and measuring information corresponding to one or more stains of the second stain composition in the biological sample, where the one or more stains comprise a fluorescent label; generating a first image of the biological sample, where the first image corresponds to a pattern of simulated hematoxylin staining in the biological sample; and generating a second image of the biological sample, wherein the second image corresponds to localization of the fluorescent label in the biological sample.

Embodiments of the methods can include any one or more of the following features.

The fluorescent counterstain can include curcumin. The fluorescent counterstain can include carmine. The methods can include before applying the second stain composition to the biological sample, applying a third stain composition to the biological sample, where the third stain composition includes eosin. The methods can include, before applying the second stain composition to the biological sample, applying a third stain composition to the biological sample, where the third stain composition comprises indigo carmine.

The first image can correspond to a pattern of simulated hematoxylin and eosin staining in the biological sample. The first image can correspond to a pattern of simulated eosin staining and simulated hematoxylin staining in the biological sample.

Removing the fluorescent counterstain can include exposing the biological sample to an antigen retrieval agent. The methods can include removing the fluorescent counterstain and eosin by exposing the biological sample to an antigen retrieval agent. The methods can include removing the fluorescent counterstain and indigo carmine by exposing the biological sample to an antigen retrieval agent.

The first stain composition can include a fixative agent. The fixative agent can include potassium aluminum sulfate dodecahydrate.

The methods can include generating the first image prior to applying the second stain composition to the biological sample. The methods can include generating the first image based on the information corresponding to the one or more stains of the first stain composition in the biological sample. The methods can include determining the second stain composition based on the first image. The methods can include identifying a set of one or more locations in the biological sample in which to identify a target analyte based on the first image.

The methods can include annotating the first image before applying the second stain composition to the biological sample. The methods can include annotating the first image during application of the second stain composition to the biological sample.

The fluorescent label can be linked to a probe for a target within the biological sample. The target can include at least one of an antigen, a peptide, and a protein. The probe can include an antibody or antibody fragment. The target can include a ribonucleic acid or a deoxyribonucleic acid.

The second stain composition can include multiple different fluorescent labels each linked to a probe for a different target within the biological sample. The second stain composition can include at least 3 different fluorescent labels (e.g., at least 5 different fluorescent labels).

The methods can include generating one or more additional images of the biological sample, each of the additional images corresponding to localization of one or more of the different fluorescent labels in the biological sample.

Applying the second stain composition to the sample can include: (a) applying a first binding agent to the biological sample, where the first binding agent includes a probe that binds to a target in the sample and a nucleic acid sequence linked to the probe; and (b) applying a first labeling agent to the biological sample, where the first labeling agent includes a nucleic acid sequence and the fluorescent label linked to the nucleic acid sequence, and where the first labeling agent hybridizes selectively to the first binding agent. The methods can include measuring fluorescence emission information from the fluorescent label.

The methods can include in step (a) applying a plurality of different first binding agents to the biological sample, where each different first binding agent includes a probe that binds to a different target in the sample and a different nucleic acid sequence linked to the probe. The methods can include, after measuring the fluorescence emission information, removing the first labeling agent from the biological sample. The methods can include applying a second labeling agent to the biological sample, where the second labeling agent includes a nucleic acid sequence and a second fluorescent label linked to the nucleic acid sequence, where the second fluorescent label is different from the fluorescent label of the first labeling agent, and where the second labeling agent hybridizes selectively to a second binding agent in the sample different from the first binding agent. The methods can include measuring fluorescence emission information from the second fluorescent label.

Generating the first image can include measuring fluorescence emission information for the fluorescent counterstain in the biological sample. Generating the first image can include measuring fluorescence emission information for the fluorescent counterstain in the biological sample and measuring absorption of incident radiation by eosin in the biological sample. Generating the first image can include measuring fluorescence emission information for the fluorescent counterstain in the biological sample and measuring absorption of incident radiation by indigo carmine in the biological sample.

Embodiments of the methods can also include any of the other features disclosed herein, including combinations of features individually described in connection with different embodiments, in any order or combination except as expressly stated otherwise.

In another aspect, the disclosure features methods that include: applying a first stain composition to a biological sample that includes at least one of curcumin and carmine lake; applying a second stain composition to the biological sample that includes at least one of eosin and indigo carmine; measuring image information corresponding to the first and second stain compositions in the biological sample; exposing the biological sample to at least one antigen retrieval agent to remove the at least one of curcumin and carmine lake and the at least one of eosin and indigo carmine from the biological sample; applying a third stain composition to the biological sample, where the third stain composition includes a fluorescent label; measuring image information corresponding to the third stain composition in the biological sample; and generating a first image based on the image information corresponding to the first and second stain compositions in the biological sample that represents a hematoxylin and eosin staining distribution in the biological sample.

Embodiments of the methods can include any of the features disclosed herein, including combinations of features individually described in connection with different embodiments, in any order or combination except as expressly stated otherwise.

In another aspect, the disclosure features methods that include: applying a first stain composition to a biological sample, and measuring information corresponding to one or more stains of the first stain composition in the biological sample, where the one or more stains include a fluorescent counterstain; generating a first image of the biological sample, where the first image corresponds to a pattern of simulated hematoxylin staining in the biological sample; removing the fluorescent counterstain from the biological sample; and performing a further analysis of the biological sample by exposing the biological sample to one or more reagents and identifying at least one analyte in the biological sample.

Embodiments of the methods can include any one or more of the following features.

The at least one analyte can be selected from the group consisting of proteins, peptides, antibodies, and antigens. The at least one analyte can be selected from the group consisting of ribonucleic acids and deoxyribonucleic acids. The at least one analyte can be a carbohydrate.

The fluorescent counterstain can include at least one of curcumin and carmine lake.

Removing the fluorescent counterstain can include exposing the biological sample to at least one antigen retrieval agent. Removing the fluorescent counterstain can include exposing the biological sample to a peroxide.

Embodiments of the methods can also include any of the other features disclosed herein, including combinations of features individually described in connection with different embodiments, in any order or combination except as expressly stated otherwise.

In another aspect, the disclosure features reagent kits that include: a first stain composition featuring a fluorescent counterstain; a fluorescent counterstain removal agent; a second stain composition featuring a fluorescent label; and a set of instructions for performing any of the methods described herein.

Embodiments of the kits can include one or more of the following features.

The fluorescent counterstain can include at least one of curcumin and carmine lake. The removal agent can include at least one of an antigen retrieval agent and a peroxide.

The kits can include a third stain composition featuring an absorptive stain. The absorptive stain can include at least one of eosin and indigo carmine.

Embodiments of the kits can also include any of the other features disclosed herein, including combinations of features individually described in connection with different embodiments, in any order or combination except as expressly stated otherwise.

Some embodiments described herein relate to a computer storage product with a nontransitory computer-readable medium (also can be referred to as a non-transitory processor-readable medium) having instructions or computer code thereon for performing various computer-implemented operations. The computer-readable medium (or processor-readable medium) is nontransitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Definitions

As used herein, a "stain" is a compound that binds to a biological sample and generates a measurable signal in the sample which can be used to determine where the stain is located in the sample. A stain can be a fluorescent compound or moiety that generates fluorescence emission when exposed to radiation. Fluorescent compounds or moieties are also interchangeably referred to as fluorescent "labels". A stain can be a chromogenic compound or moiety that absorbs certain wavelengths of incident radiation and does not absorb other wavelengths of incident radiation. A stain can be non-specific, such that it does not bind or localize with a particular type of target molecule, structure, or compartment within a sample. Examples of such non-specific stains are "counterstains". A stain can be specific, and can bind to or localize with a particular type of target molecule, structure, or compartment within as ample. Examples of specific stains are DAPI (which binds to DNA), antibody-linked stains (e.g., fluorescent moieties linked directly or indirectly to antibodies that bind specifically to particular antigens such as tumor markers in a sample), and nucleic acid-linked stains (e.g., fluorescent moieties linked directly or indirectly to oligonucleotides that bind specifically to particular nucleic acid targets in a sample, such as different RNA species).

As used herein, "hematoxylin" refers to the chemical compound $C_{16}H_{14}O_6$, which is commonly used as a histological stain. The term "hematoxylin" should also be understood to encompass chemical derivatives of hematoxylin that contain substituent modifications at one or more ring positions of the hematoxylin structure, and which do not substantially change the manner in which the modified structure localizes in biological samples. Substituents that can be modified, added, or removed in the chemical derivatives include alkyl groups, alkene groups, alkyne groups, hydroxyl groups, halide groups, cyanate groups, isocyanate groups, thiocyanate groups, isothiocyanate groups, amide groups (primary, secondary, and tertiary), amine groups, alkoxy groups, thioalkoxy groups, thiol groups, phosphate groups, sulfate groups, ester groups, aldehyde groups, ketone groups, and carboxylic acid groups.

As used herein, "eosin" refers to a fluorescent compound that derived from fluorescein, and is commonly used as a histochemical stain. The term "eosin" should be understood to encompass all eosin compounds which are derivatives of one another, including (but not limited to) eosin Y (also referred to as eosin Y ws, eosin yellowish, Acid Red 87, bromoeosine, bromofluoresceic acid, D&C Red No. 22), and eosin B (also referred to as eosin bluish, Acid Red 91, Saffrosine, Eosin Scarlet, and imperial red). Eosin Y is a tetrabromo derivative of fluorescein, while eosin B is a dibromo dinitro derivative of fluorescein. Derivatives also encompass chemical derivatives of eosin that contain substituent modifications at one or more ring positions of the eosin structure, and which do not substantially change the manner in which the modified structure localizes in biological samples. Substituents that can be modified, added, or removed in the chemical derivatives include alkyl groups, alkene groups, alkyne groups, hydroxyl groups, halide groups, cyanate groups, isocyanate groups, thiocyanate groups, isothiocyanate groups, amide groups (primary, secondary, and tertiary), amine groups, alkoxy groups, thioalkoxy groups, thiol groups, phosphate groups, sulfate groups, ester groups, aldehyde groups, ketone groups, and carboxylic acid groups.

As used herein, a "hematoxylin analog" is a reagent or reagent composition that, when introduced into a sample, localizes in the sample with a distribution pattern that is similar to hematoxylin. As such, a measured signal corresponding to the hematoxylin analog represents the distribution pattern that would be observed if hematoxylin was introduced into the sample and a signal corresponding to the hematoxylin was measured.

As used herein, an "eosin analog" is a reagent or reagent composition that, when introduced into a sample, localizes in the sample with a distribution pattern that is similar to eosin. As such, a measured signal corresponding to the eosin analog represents the distribution pattern that would be observed if eosin was introduced into the sample and a signal corresponding to the eosin was measured.

As used herein, "curcumin" refers to the compound curcumin, $C_{21}H_{20}O_6$. Curcumin can exist in enol or keto form, and the term "curcumin" refers to both forms. In addition, the term "curcumin" encompasses chemical derivatives of curcumin that contain substituent modifications at one or more phenyl ring positions, one or more double-bonded carbon atoms, and/or one or more single-bonded carbon atoms, of the curcumin structure, and which do not substantially change the manner in which the modified structure localizes in biological samples. Substituents that can be modified, added, or removed in the chemical derivatives include alkyl groups, alkene groups, alkyne groups, hydroxyl groups, halide groups, cyanate groups, isocyanate groups, thiocyanate groups, isothiocyanate groups, amide groups (primary, secondary, and tertiary), amine groups, alkoxy groups, thioalkoxy groups, thiol groups, phosphate groups, sulfate groups, ester groups, aldehyde groups, ketone groups, and carboxylic acid groups.

As used herein, "carmine" refers to a pigment produced from carminic acid. Carmine is also referred to as cochineal, cochineal extract, crimson lake, carmine lake, and natural red 4. The term carmine also encompasses chemical derivatives of the carmine structure that contain substituent modifications at one or more ring positions and/or one or more aliphatic carbon atoms of the carmine structure, and which do not substantially change the manner in which the modified structure localizes in biological samples. Substituents that can be modified, added, or removed in the chemical derivatives include alkyl groups, alkene groups, alkyne groups, hydroxyl groups, halide groups, cyanate groups, isocyanate groups, thiocyanate groups, isothiocyanate groups, amide groups (primary, secondary, and tertiary), amine groups, alkoxy groups, thioalkoxy groups, thiol groups, phosphate groups, sulfate groups, ester groups, aldehyde groups, ketone groups, and carboxylic acid groups.

As used herein, "indigo carmine" refers to the compound disodium [2(2')E]-3,3'-dioxo-1,1',3,3'-tetrahydro[2,2'-biindolylidene]-5,5'-disulfonate. The term indigo carmine also encompasses chemical derivatives of the indigo carmine structure that contain substituent modifications at one or more ring positions, and which do not substantially change the manner in which the modified structure localizes in biological samples. Substituents that can be modified, added, or removed in the chemical derivatives include alkyl groups, alkene groups, alkyne groups, hydroxyl groups, halide groups, cyanate groups, isocyanate groups, thiocyanate groups, isothiocyanate groups, amide groups (primary, secondary, and tertiary), amine groups, alkoxy groups, thioalkoxy groups, thiol groups, phosphate groups, sulfate groups, ester groups, aldehyde groups, ketone groups, and carboxylic acid groups.

As used herein, a "H&E image" of a biological sample refers to an image of the sample that has been stained with both hematoxylin and eosin, and shows the localization of both stains in the sample. In an H&E image, cytoplasm typically appears pink-orange in color and nucleic typically appear blue or purple. However, it should be understood more generally that the term "H&E image" refers to an image in which contrast between tissue morphological and constituent features is similar to the contrast that would be observed when the sample is stained with hematoxylin and eosin, regardless of the particular colorization of the image.

As used herein, a "simulated H&E image" refers to an image of a sample that is computationally generated, and that represents how the sample would appear if the sample was stained with hematoxylin and eosin. In other words, a simulated H&E image is a computationally generated H&E image for a sample. Typically, the simulated H&E image is generated for a sample to which hematoxylin, eosin, or both hematoxylin and eosin, have not been applied.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Introduction

Figure 1:
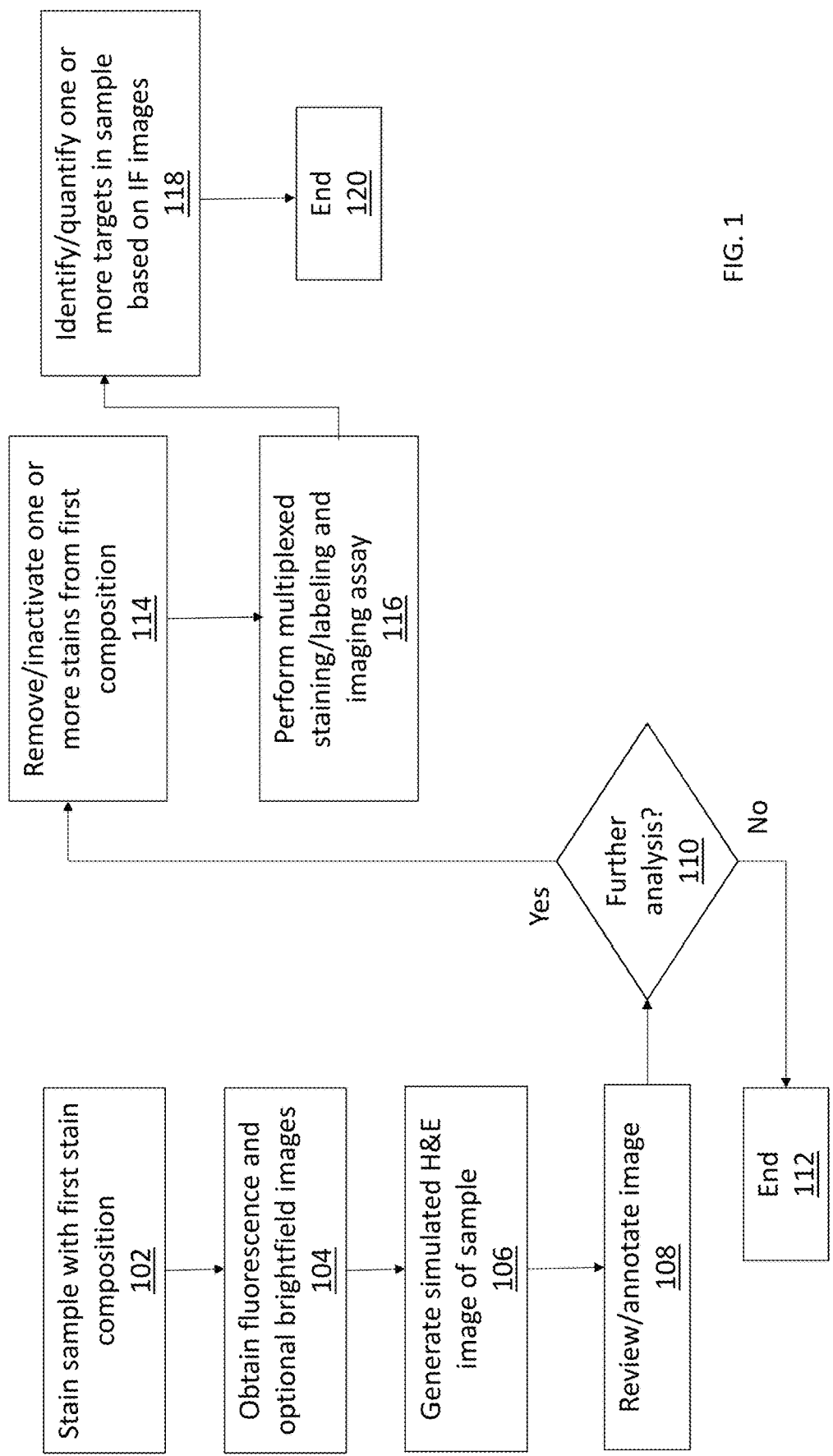
FIG. 1 is a flow chart showing a set of example steps for analyzing a tissue sample.

Methods such as DAB-based immunohistochemical staining of tissue samples provide a view of just one target analyte in a tissue sample, so that several tissue sections are typically used to assess a plurality of targets. Because sequential tissue sections contain different individual cells, it is often not possible to determine the status of multiple targets in a given cell using such methods.

Recent multiplexed imaging techniques, including multiplexed immunofluorescent (mIF) imaging, have enabled the analysis of many target species (e.g., antigens, RNAs) in a single tissue sample. Such techniques are a significant improvement over single-target methods. In a single imaging step, up to 8 targets can be simultaneously measured using a combination of suitably chosen stains and computational processing methods such as spectral unmixing to separate measured fluorescent signals corresponding to the different stains. Stains that are suitable for such methods include, for example, the Opal® reagents, available from Akoya Biosciences (Menlo Park, CA). Alternately, suitable stains include the UltiMapper I/O PD-L1 kit, the UltiMapper I/O Immuno8 kit, or InSituPlex stains (available from Ultiview Inc., Cambridge MA). Multiplexed staining, imaging and spectral umixing methods are described for example in the following U.S. patents and patent application publications, the entire contents of each of which are incorporated herein by reference: U.S. Pat. Nos. 7,555,155; 8,462,981; 8,330,087; 9,541,504; 10,126,242; and US 2019/0339203.

Sequential imaging cycles can also be performed to further increase the number of target analytes that can be interrogated. For example, following each cycle of staining and imaging, stains applied to the sample can be removed or inactivated, and a new cycle of staining and imaging can be initiated in which a new set of stains is introduced, and one or more images of the newly introduced stains are obtained. Such methods can be particularly useful for assays that investigate a large number of target analytes. One example of such an assay is an antigen-targeting assay that targets a panel of tumor-related markers in a tissue sample. Another example of such an assay is a RNA assay that investigates transcripts in particular regions or cells of a tissue sample. RNA assays, in particular, may investigate hundreds or even thousands of different transcript species, and therefore benefit from multiple imaging cycles.

Suitable reagents for performing sequential imaging cycles include, for example, the CODEX® reagents available from Akoya Biosciences. Aspects of multi-cycle labeling and imaging of target analytes in biological samples are described for example in the following patents and patent publications, the entire contents of each of which are incorporated herein by reference: U.S. Pat. Nos. 9,909,167; 10,370,698; WO 2021/067475; WO 2020/163397; and WO 2021/127637.

In many circumstances, including clinical settings and in pharmaceutical drug trials, tissue samples are small, which forces triage decisions about how to best utilize scarce biological material from such samples. Automated staining processes are widely used in research and clinical practice, because they make it practical to process large numbers of samples reliably, repeatably, and economically. Automated processes can reduce waste associated with manual sample handling and processing.

However, even when automated sample processing methods are used, triage decisions may still be necessary. For example, decisions may be made as to whether to proceed or not proceed with a full preparation and staining/labeling of a sample, which commits the sample and removes it from the pool of biological material available for other assays. Such decisions can be helpfully guided by reference to a hematoxylin and eosin (H&E) image of the sample. That is, by staining the sample with H&E, sample morphology and structural features can be reviewed by a pathologist, and the pathologist can determine whether a full preparation and staining of a section of the sample for further analysis is warranted. This conditional assessment eliminates or reduces the severity of the triage decisions one must make with scarce sample material, and avoids costly and time-consuming multispectral (e.g., mIF) preparation and imaging for samples where such analysis is unsuitable or unwarranted.

Unfortunately, conventional brightfield staining with H&E interferes with many kinds of subsequent processing such as mIF, genomic analysis such as FISH, and RNA analysis. In particular, hematoxylin has spectral properties that interfere with multiplexed fluorescence imaging of samples, obscuring signals that correspond to particular target analytes. Further, hematoxylin—once applied to the sample—is difficult to remove, making it difficult to chemically inactivate contributions from hematoxylin in later fluorescence images that are acquired.

To address the foregoing and other difficulties associated with H&E imaging of biological samples, this disclosure features methods, systems, reagents, and kits for generating simulated H&E images of biological samples. Samples are exposed to a "hematoxylin analog" and/or eosin or an "eosin analog". The hematoxylin analog is a reagent or reagent composition that localizes in the sample and produces an optical signal that is similar to, and representative of, the signal that would be produced by hematoxylin in the sample. The eosin analog, if present, is a reagent or reagent composition that localizes in the sample and produces an optical signal that is similar to, and representative of, the signal that would be produced by eosin in the sample Images of the sample are obtained, and include contributions from the hematoxylin analog and/or eosin or the eosin analog. A simulated H&E image of the sample can then be generated from these measured contributions. Subsequent sample processing steps can optionally include antigen retrieval, and a multiplexed staining and imaging protocol (e.g., a multiplexed immunofluorescence histochemistry protocol, or a multiplexed RNA labeling and fluorescence detection protocol).

The simulated H&E image of the sample can be used in a variety of ways. In some embodiments, for example, the simulated H&E image can be used to determine whether to perform the multiplexed staining and imaging protocol, based on the observed sample features in the simulated H&E image. In certain embodiments, the simulated H&E image can be used to select certain regions of the sample for analysis via the multiplexed staining and imaging protocol, and even to guide delivery of reagents to the selected regions of the sample. In some embodiments, the simulated H&E image can be used to assess the sample quality generally. In certain embodiments, the simulated H&E image can be used together with image information from the multiplexed staining and imaging protocol to classify particular regions of the sample into different morphological, pathological, or disease-state classes.

As will be discussed in further detail below, in some embodiments, the simulated H&E image is obtained from a sample that has been stained with a dilute concentration of eosin, and curcumin or carmine, which function as a hematoxylin analog. Both curcumin and carmine typically localize in the sample with a distribution pattern that is similar to hematoxylin, and therefore measured fluorescence signals corresponding to either curcumin or carmine represent the expected distribution pattern of hematoxylin, and can be used to generate the simulated H&E image.

An important advantage of the methods, systems, reagents, and kits described herein is that staining of a tissue sample with a hematoxylin analogue and eosin or an eosin analog does not interfere with subsequent processing and analysis of that same tissue section using multispectral staining/labeling and imaging techniques such as mIF. Image signals measured during later staining/labeling and imaging steps are either not affected at all by creating the simulated H&E image, or the effects on signal strength or epitope availability are minor and can be accommodated during assay interpretation.

Another important advantage of the methods, systems, reagents, and kits described herein is that the simulated H&E image and image information from multispectral staining/labeling and imaging protocols correspond to the exact same sample, rather than from sequential tissue sections cut from the same block. Sequential tissue sections can be subject to differences in handling. Furthermore, as explained above, sequential tissue sections typically contain different cells, making single-cell comparisons more difficult. Generating a simulated H&E image and multispectral image information from the same tissue section avoids these difficulties.

In some embodiments, the simulated H&E image can be generated prior to performing additional sample processing and imaging steps. Clinical practice and research studies on human samples is often performed on formalin-fixed paraffin-embedded (FFPE) tissue blocks. For immunohistochemical (IHC) staining or mIF imaging, one or more antigen retrieval (AR) steps may be necessary or desirable prior to introducing IHC or IF stains. However, the AR step can alter tissue structure or morphology and can remove chromogenic features of the tissue such as melanin. By generating the simulated H&E image of the sample prior to subsequent processing steps, the sample can be viewed as it was prior to undergoing antigen retrieval (AR) treatment.

Without wishing to be bound by theory, it is believed that the AR treatment removes the stains that were used to generate the simulated H&E image. Empirically, fluorescence signal levels after AR treatment are substantially the same as those for unstained samples that have undergone AR treatment. Residual signals due to hematoxylin analogs, eosin, and eosin analogs are nearly, or completely, eliminated. A variety of different reagents and compositions can be used for AR treatment. As one example, a tris-EDTA solution with pH 9 can be used successfully for AR. In general, because AR is a typical step in many staining workflows, removal of signals that are used to generate the simulated H&E image in such workflows does not require additional time or sample processing steps.

Methods for Sample Staining and Imaging

FIG. 1 is a flow chart that shows a set of example steps for analyzing a sample. In a first step 102, the sample is stained with a first stain composition. The first stain composition includes a hematoxylin analog, and eosin or an eosin analog. As discussed above, a variety of different hematoxylin analogs can be used, including (but not limited to) curcumin and carmine. A variety of different eosin analogs can be used, including (but not limited to) indigo carmine.

Next, in step 104, brightfield and fluorescence images of the sample are obtained. In some embodiments, the fluorescence image of the sample represents contributions from the hematoxylin analog, and represents the distribution pattern of hematoxylin in the sample that would have occurred if hematoxylin had been introduced.

In step 106, a simulated H&E image of the sample is generated, as will be discussed in greater detail below. The simulated H&E image is optionally reviewed and/or annotated by a pathologist, technician, or other person in step 108. Following review, a decision occurs in step 110 as to whether further processing/analysis of the sample is desired. This decision can be based on morphological and/or structural features of the sample that are observed in the simulated H&E image, for example. If further analysis is not desired, the procedure ends at step 112.

If further analysis is desired, then in step 114, one or more stains from the first composition can optionally be removed or inactivated. As discussed above, antigen retrieval can be performed to remove the one or more stains. It should be noted that antigen retrieval (or a similar procedure) can optionally be performed even when the target analytes in the sample are not antigens (e.g., RNA). Antigen retrieval in such circumstances can be regarded as simply a stain removal/inactivation step.

Next, in step 116, a multiplexed staining/labeling and imaging assay is performed. Such assays can include, for example, exposing the sample to probes that target one or more different types of analytes in the sample, and imaging the sample to obtain information about the localizing of the probes.

A variety of different types of probes can be introduced. In some embodiments, the probes target specific types of antigens in the sample, and consist of antibodies that are linked directly or indirectly to fluorescent moieties (e.g., "labels"). Each type of antibody can be linked to a different, spectrally distinguishable label, so that multispectral images of the sample reveal the locations of each of the different types of antibodies—and therefore their specific target antigens—in the sample. Multiple cycles of imaging and staining/labeling can optionally be performed, with optional inactivation/quenching of the previous cycle's labels before a new set of probes is introduced in the next cycle.

In certain embodiments, the probes consist of antibodies that are linked to oligonucleotides, such that each type of antibody is linked directly or indirectly to a different type of oligonucleotide. All such probes can be introduced in a single sample labeling step, or in successive labeling steps. After probes have bound to the target antigens in the sample, labeling agents are introduced. Each type of labeling agent includes an oligonucleotide that is complementary to the oligonucleotide of one of the probes, and a fluorescent moiety linked directly or indirectly to the oligonucleotide of the labeling agent. The oligonucleotides of the probe and labeling agent hybridize, localizing the labeling agent in the sample where the target analyte is located. When the sample is imaged, the locations of the labeling agents reveal the locations of the corresponding analytes. Multiple cycles of labeling and imaging can be performed. Between cycles, labeling agents from the prior art are generally removed via dehybridization from their corresponding probes prior to introduction of a new set of labeling agents.

In some embodiments, the probes consist of oligonucleotides. A first portion of the probe oligonucleotide sequence is complementary to, and binds selectively (through hybridization) to a target nucleic acid in the sample (e.g., a target RNA species). A second portion of the probe oligonucleotide contains one or more additional nucleic acid sequences that function as reporter sequences. For example, in certain workflows, the second portion of the probe oligonucleotide contains a "barcode" sequence that is complementary to an oligonucleotide of a labeling agent, as discussed above. When introduced, the labeling agent selectively hybridizes to the barcode sequence, localizing the labeling agent in the sample where the target RNA is located. By obtaining an image of fluorescence emission from the labeling moiety linked to the oligonucleotide of the labeling agent, locations of the target RNA in the sample can be determined. Multiple cycles of labeling and imaging can be performed. Between cycles, labeling agents from the prior art are generally removed via dehybridization from their corresponding probes prior to introduction of a new set of labeling agents.

Alternatively, in some workflows, the second portion of the probe oligonucleotide can contain multiple nucleic acid sequences that function as reporter moieties. Each type of reporter moiety selectively hybridizes to a different type of labeling agent, with a complementary oligonucleotide linked to a different labeling moiety. During each cycle of staining/labeling and imaging, a different set of labeling agents is introduced, with each labeling agent generating fluorescence emission in a different spectral band relative to the other labeling agents of the set. Multiple staining/labeling and imaging cycles are performed, and particular target analytes are identified and localized in the sample based on combinations of co-located fluorescence signals that are measured. Effectively, each type of RNA target corresponds to a different combination of reporter moieties and, therefore, a different combination of fluorescence signals. In this manner, a large number of different RNA targets can be assayed in combinatorial fashion with a relatively small number of different labeling agents. Additional aspects of methods for RNA target detection are described in U.S. provisional patent applications 63/171,297 and 63/189,056, the entire contents of each of which are incorporated herein by reference.

In some embodiments, the probes consist of antibodies or oligonucleotides that are linked to a catalytic agent such as horseradish peroxidase (HRP). The example is exposed to probes which selectively bind to one of the analytes (e.g., antigens, proteins, RNA), localizing the catalytic agent in the sample with the analyte. The sample is then exposed to a tyramide-linked labeling agent. The catalytic agent catalyzes activation of the tyramide and deposition of the labeling agent in the sample in proximity to the target analyte. The deposited labeling agent is imaged (e.g., by measuring fluorescence emission), which identifies the target analyte in the sample. The deposited labeling agent can then be removed or inactivated, and another cycle of labeling and imaging performed to identify another target analyte.

As discussed above, in step 118, using the multispectral image information obtained in step 116, the target analytes (e.g., antigens, RNA) in the sample are identified and optionally quantified based on the relative intensities of the measured fluorescence signals. The procedure ends at step 120.

Some or all of the foregoing sample processing steps can optionally be performed in an automated stainer such as a Leica Bond (available from Leica Biosystems, Buffalo Grove IL). A variety of other automated strainers can be also be used, and any one or more of the steps in FIG. 1 can also be performed manually.

In step 114, the AR treatment can be performed by exposing the sample to the Leica ER2 reagent (available from Leica Biosystems). Alternatively, or in addition, AR processing can be performed by heating the sample in a pressure cooker such as the 6-quart Instant Pot Duo 7-in-1 Electric Pressure Cooker, available from Instant Brands (Kanata, ON), or the Decloaking Chamber, available from Biocare Medical (Concord CA). Further still, AR can be performed in a microwave treatment (MWT) with a tris/EDTA solution having a pH of approximately 9.

Steps 116 and/or 118 can be performed manually, in an autostainer, or in an automated system such as the Vectra Polaris® system (available from Akoya Biosciences).

Figure 2:
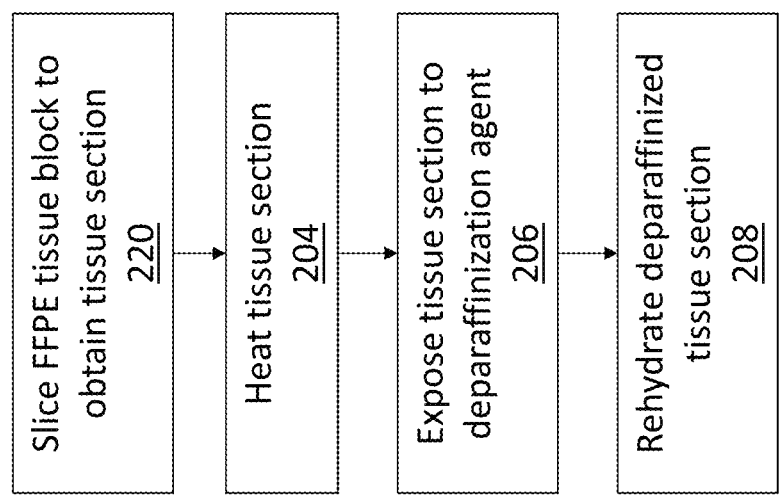
FIG. 2 is a flow chart showing a set of example steps for preparing a formalin-fixed, paraffin-embedded (FFPE) tissue section for staining and imaging.

In step 102, the sample can be contacted with first stain composition after obtaining the sample as a tissue section from a tissue block. FIG. 2 is a flow chart showing a set of example steps for obtaining a tissue section from a FFPE tissue block. In a first step 202, the FFPE tissue block is sliced (e.g., using a microtome) to obtain the tissue section. Then, in step 204, the tissue section is heated, and in step 206, the tissue section is exposed to a deparaffinization agent to dewax the tissue section. After dewaxing, the deparaffinized tissue section is rehydrated in step 208 to yield a tissue section that can be stained. The foregoing steps are generally well known in the art, and conventional methods can be used for each of the steps in FIG. 2.

Returning to FIG. 1, in step 102, the sample can optionally be contacted with the hematoxylin analog and eosin or the eosin analog at different times. For example, in some embodiments, an aqueous solution of curcumin and/or carmine and a dye fixative (e.g., a mordant) such as potassium aluminum sulfate dodecahydrate first contact the sample. The sample can be contacted with the solution for approximately 30 minutes. The sample can then be dehydrated through gradient alcohol, and then stained with a dilute eosin solution. As an example, a suitable solution includes ethanol to which has been added 0.0001% eosin Y by weight and 0.005% glacial acetic acid by weight. After staining, the sample can be dried with xylene, a coverslip can be mounted, and the sample can be imaged in a fluorescent imaging system. One or more images of the sample are obtained, which contain signals that correspond to the hematoxylin analog (e.g., curcumin and/or carmine) and eosin or the eosin analog (e.g., indigo carmine). The simulated H&E image is generated from the measured fluorescence signal information, as will be discussed in greater detail below.

Eosin Y formulations including alum can be used as a counterstain in the first stain composition. In some embodiments, for example, both the hematoxylin analog (e.g., carmine) and eosin Y can be prepared separately by heating to 80° C. in solution with potassium alum. Sample drying steps can be eliminated in this manner prior to attaching a coverslip.

To attach a coverslip, a mounting medium such as H&E Mount (available from Innovex Biosciences, Richmond, CA) can be used to attach a coverslip from aqueous solution. After imaging the sample to obtain the simulated H&E image, the coverslip can be removed.

Figure 3:
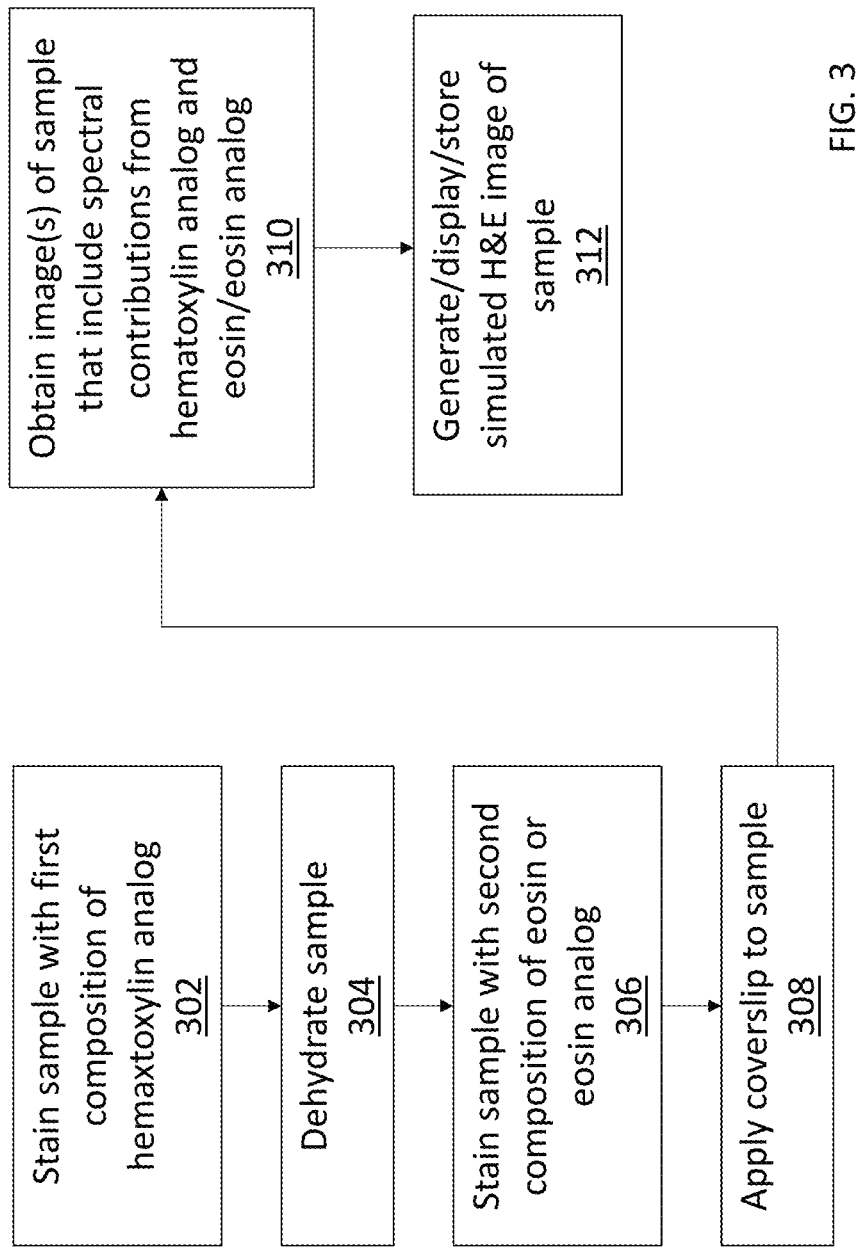
FIG. 3 is a flow chart showing a set of example steps for generating a simulated H&E image of a tissue sample.

FIG. 3 is a flow chart that shows a set of example steps for generating a simulated H&E image of a tissue sample. In a first step 302, the sample is stained with a first composition that includes a hematoxylin analog. Examples of suitable hematoxylin analogs include, but are not limited to, curcumin and carmine. Next, in step 304, the sample is dehydrated, e.g., using xylene in a conventional drying protocol.

Then, in step 306, the sample is stained with a second composition that includes eosin or an eosin analog (e.g., indigo carmine). A coverslip is applied to the sample in step 308, and one or more images of the sample that include spectral contributions from both the hematoxylin analog and eosin or the eosin analog are obtained in step 310. These images are used in step 312 to generate, and optionally display and/or store, a simulated H&E image of the sample. The image can be viewed, annotated, and used as described herein to take further action, such as to assess whether the sample should be further analyzed in a multispectral staining/labeling and imaging protocol. The image can also be used to identify particular regions of interest in a sample, which are then analyzed computationally following the multispectral staining/labeling and imaging protocol. Any of the additional steps described herein, including antigen retrieval, and multispectral staining/labeling and imaging, can be performed.

Figure 8:
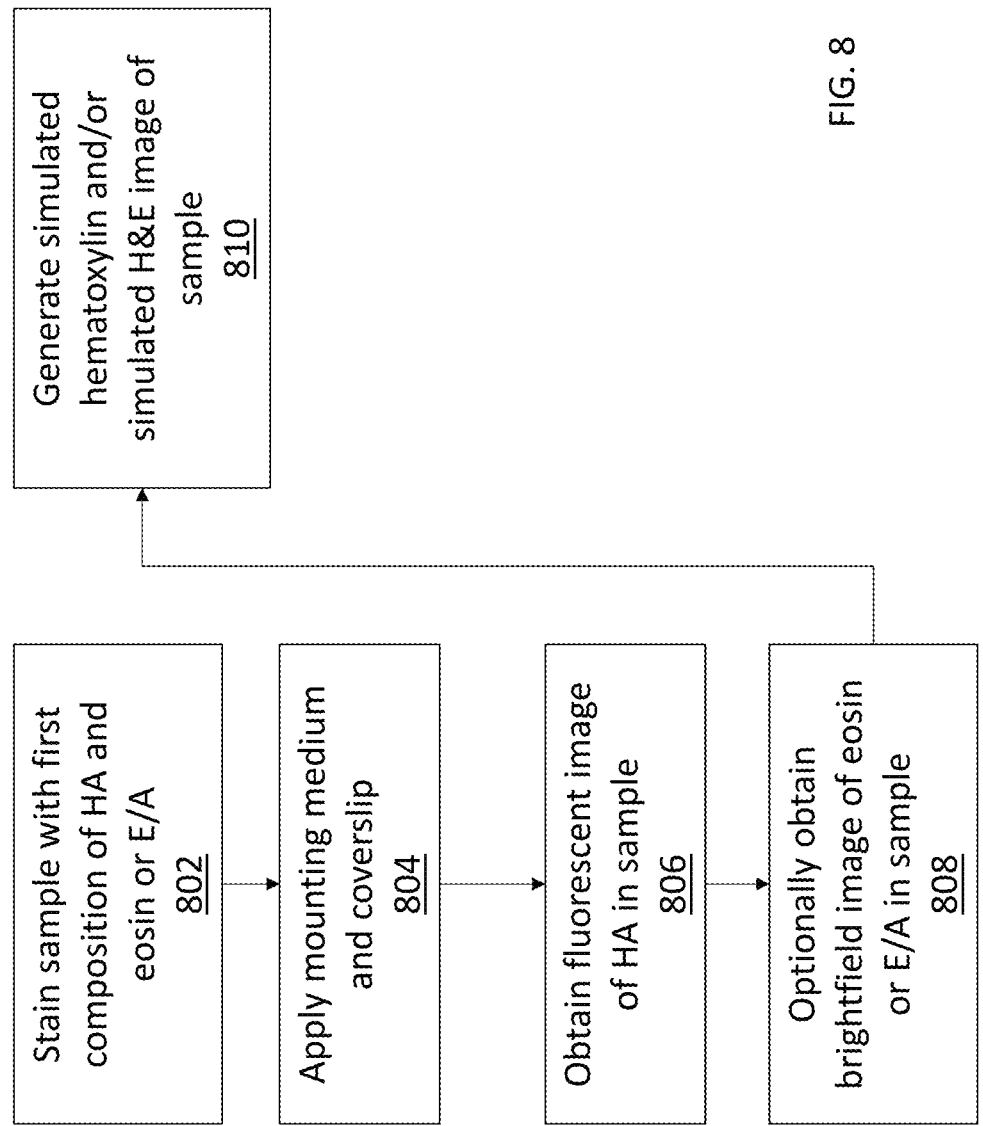
FIG. 8 is a flow chart showing a set of example steps for analyzing a tissue sample.

FIG. 8 is a flow chart that shows another set of example steps for generating a simulated H&E image of a tissue sample. In a first step 802, the sample is stained with a composition that includes a hematoxylin analog and eosin or an eosin analog. Examples of suitable hematoxylin analogs include, but are not limited to, curcumin and carmine. An example of a suitable eosin analog is indigo carmine. Next, in step 804, a mounting medium and coverslip is applied to the sample.

In step 806, a fluorescent image of the hematoxylin analog is obtained. In step 808, a brightfield image of eosin or the eosin analog is optionally obtained. Then, in step 810, either or both of a simulated hemaxtoxylin image (generated from the image of step 806) and a simulated H&E image (generated from the images of steps 806 and 808) are generated and optionally displayed and/or stored. As described above, the image can be viewed, annotated, and used as described herein to take further action, such as to assess whether the sample should be further analyzed in a multispectral staining/labeling and imaging protocol. The image can also be used to identify particular regions of interest in a sample, which are then analyzed computationally following the multispectral staining/labeling and imaging protocol. Any of the additional steps described herein, including antigen retrieval, and multispectral staining/labeling and imaging, can be performed.

In general, following staining with the hematoxylin analog and dilute eosin, the color of the sample appears nearly unchanged, due to the low concentrations and inherent properties of the stains. Nonetheless, samples may have some inherent absorption due to melanin, bilirubin, red blood cells, and other features.

As described above, in some embodiments, the simulated H&E image is generated based on both a fluorescent image and a transmitted-light brightfield image of the sample, and the simulated H&E image includes chromogenic features such as melanin. The brightfield image of the sample can be registered with the fluorescent image to create a simulated H&E image that incorporates information about absorptive features in the sample.

In some embodiments, particularly for digital pathology, a slide scanner is used to obtain sample images. The scanner produces whole-slide, simulated H&E images. A pathologist or other person familiar with H&E images can reviews the image and take a number of actions including providing annotations to the digital pathology, such as an overall decision to proceed or halt further analysis on this sample, and/or regions to include or exclude from subsequent analysis, and/or the identity of regions in the sample that constitute one or more features such as a tumor margin or other structures of interest. The set of annotations, and details about the review such as the identity of the reviewer, time of the review, or other information, can be recorded in a laboratory information system to facilitate the overall workflow.

The methods and systems described herein can implement workflows in which multispectral images of the sample are analyzed together with the simulated H&E image. For example, both the simulated H&E image and the multispectral sample images can be displayed to a user (e.g., side-by-side, overlaid, or alternating between these images), along with quantitative metrics derived from the images such as cell locations, density maps, and co-located target analytes.

Simulated H&E Image Generation

To generate a simulated H&E image from image information corresponding to a hematoxylin analog and eosin or an eosin analog, target colors are chosen for hematoxylin and eosin. These correspond to the hues that the simulated H&E image will have for nuclear chromatin and extracellular material; they are a deep blue or purple and a vivid pink, respectively. Each hue is represented by an RGB triple, representing the red, green, and blue content in that color.

For each pixel, a signal is created by assessing the hematoxylin analog (HA) signal and eosin or eosin analog (E/A) signal in that pixel. These are scaled based on an image-wide assessment of what is strong staining for that component, based on exposure level, overall staining intensity, and similar factors, to yield a relative (scaled) HA signal and a relative E/A signal. Using these, a simulated brightfield image is created by starting with a white signal; multiplying by a scaled color contribution for HA based on the hematoxylin hue; and further multiplying by a scaled color contribution for E/A based on the eosin hue.

It is common in computational image processing to represent RGB values on a 0-255 scale. White is represented by an RGB triple of {250, 250, 250}, the hematoxylin hue can be represented by RGB values of {117, 88, 155}, and the eosin hue can be represented by {252, 154, 208}.

A look-up table is created for each component, representing the color contribution associated with signals of varying scaled strength s in that signal.

Each component C has RGB values $R_c$, $G_c$, and $B_c$, and a look-up table (LUT) is calculated with R, G, and B values as a function of normalized signal s, given by:

$$LUT_C(s, R) = 255 * \left(\frac{R_C}{255}\right)^s \quad [1a]$$

$$LUT_C(s, G) = 255 * \left(\frac{G_C}{255}\right)^s \quad [1b]$$

$$LUT_C(s, B) = 255 * \left(\frac{B_C}{255}\right)^s \quad [1c]$$

The LUTs are calculated once per image, and HA and E/A signals are scaled down so that pixels strongly stained with a given component have a scaled strength of order 1 for that component.

Then the RGB color triple is calculated for every pixel by multiplying the color triple for the chosen white color by the LUT color triple for the scaled HA signal at that pixel, and the LUT color triple for the scaled E/A signal at that pixel. Multiplying by a color triple means multiplying the individual R, G, and B values, and dividing by the full-scale of 255:

$$R = R_{White} * \frac{LUT_{Carmine}(s, R)}{255} * \frac{LUT_{Eosin}(s, R)}{255} \quad [2a]$$

$$G = G_{White} * \frac{LUT_{Carmine}(s, G)}{255} * \frac{LUT_{Eosin}(s, G)}{255} \quad [2b]$$

$$B = B_{White} * \frac{LUT_{Carmine}(s, B)}{255} * \frac{LUT_{Eosin}(s, B)}{255} \quad [2c]$$

When a brightfield image (BF) is acquired, then image has R, G, and B values corresponding to the visual appearance of the sample at each pixel. This brightfield image is spatially registered with the fluorescent image, so that the same pixel in the image array corresponds to the same location in the sample. An image is produced with R, G, and B values at each pixel calculated using the following equations:

$$R = R_{White} * \frac{LUT_{Carmine}(s, R)}{255} * \frac{LUT_{Eosin}(s, R)}{255} * \frac{R_{BF}}{255} \quad [3a]$$

$$G = G_{White} * \frac{LUT_{Carmine}(s, G)}{255} * \frac{LUT_{Eosin}(s, G)}{255} * \frac{G_{BF}}{255} \quad [3b]$$

$$B = B_{White} * \frac{LUT_{Carmine}(s, B)}{255} * \frac{LUT_{Eosin}(s, B)}{255} * \frac{B_{BF}}{255} \quad [3c]$$

The brightfield image can be considered to represent the transmission of the sample in the RGB color bands where a value of 255 indicates full transmission, which multiplies the image from Equation 2 by the sample transmission on a pixel-by-pixel basis.

Samples stained with carmine and eosin showed strong eosin Y emission in the Opal 520 and Opal 570 channels and were undetectable in the Opal 620 channel. Carmine emitted strongly in the Opal 620 channel, moderately in the autofluorescence (AF) channel, weakly in the Opal 570 and 690 channels, and was undetectable in the Opal 520 channel. Based on that, Opal 520 signal was attributed to eosin Y, and Opal 620 signal was attributed to carmine. The signals in these bands were used to generate the simulated H&E image as described above.

Samples stained with dilute curcumin and eosin Y showed strong eosin Y emission in the Opal 520 and Opal 570 channels. Curcumin emitted strongly in the Opal 480 and AF channels, weakly in the Opal 520 and DAPI channels, but was not substantial in the Opal 570 channel. Based on that, Opal 570 signal was attributed to eosin Y, and Opal 480 signal was attributed to curcumin. The signals in these bands were used to generate the simulated H&E image as described above.

Other sets of fluorescent imaging filters may be used. Selection of the filters can be made based on factors such as to the imaging system, and the fluorescent properties of eosin or the eosin analog and the hematoxylin analog. Two fluorescent imaging bands can be used to construct the simulated H&E image. More than two fluorescent imaging bands can also be used, and ratios, sums or differences of these bands calculated from them; or multispectral techniques such as spectral unmixing employed; to isolate signals or remove sample autofluorescence. Functionally, provided that signals corresponding to each of the species (i.e., the hematoxylin analog and eosin or the eosin analog) can be distinguished, the simulated H&E image can be generated.

Analysis of Images

In some embodiments, the simulated H&E image and the multispectral images are obtained using separate workflows. In certain embodiments, a laboratory information management system (LIMS) is used to associate them but the analysis or interpretation of each image occurs separately. In some embodiments, the workflow tightly couples the two types of images in ways as described below.

Once the simulated H&E view is generated, it can be reviewed. This review can include assessment of the sample generally, its aptness for subsequent multispectral labeling and imaging analysis, the sample extent and the types of structures of interest, and so forth. A reviewer may attach annotations to the image, such as: an approval to proceed; indication of regions of interest for subsequent analysis or regions to exclude from analysis; and the identity of the reviewer. The review and the annotation functions can be done using digital pathology tools for whole-slide viewing and annotation.

In some embodiments, this review is performed before multispectral sample processing (e.g., staining/labeling and imaging), and an assessment is made whether to proceed with such processing or not. That avoids the expense and effort of performing these steps for samples that are rejected based on the simulated H&E image alone.

Sometimes, this review includes recording annotations that are used to direct subsequent image analysis of the multispectral imaging data. The subsequent assessment can be made by a different party than the first assessment of whether to proceed with sample staining/labeling and imaging or not. For example, the first decision may be made by a histologist and the second may be made by a pathologist. Either or both can be made remotely, using digital pathology tools.

Once annotations have been made to guide subsequent image analysis, a lab can proceed with sample staining/labeling, imaging, image analysis, and scoring steps without further intervention by a sample expert such as a researcher or pathologist. The overall number of intervention points can be reduced to include this initial assessment, and then an interpretation of the sample results.

Because the annotations to guide image processing are made on the simulated H&E images, they can be done while the sample is undergoing subsequent staining/labeling or multispectral imaging, and the sample can proceed directly to image analysis as soon as its multispectral imaging is complete. This saves time and simplifies scheduling, compared with workflows where the equivalent annotations are performed on the multispectral images.

When annotations are made to the simulated H&E image of the sample for use in further processing the sample, it is valuable to be able to transform between the coordinate systems of the two images. That enables regions drawn on one image to be properly placed on the other image.

This is a similar technical problem to that of registering images of similar but distinct samples, such as arises when processing serial sections cut from a tissue block. Techniques suitable for that application can also be used here. Image registration is generally less challenging because the images described herein are of the same sample, taken after it has been immobilized on a slide. While there can be slight morphological changes due to AR and sample labeling with multiple probes, there is nonetheless a high degree of similarity between the features recorded in the two images. For many purposes one can treat the sample as a rigid-body and use simple coordinate operations such as translation and rotation to transform from one image space to another.

Multiplexed Assays for Target Analytes

After the sample has been stained and imaged to produce a simulated H&E view, and AR treatment has been performed, the sample can be processed using a variety of multiplexed staining/labeling and multispectral imaging techniques, according to the nature of the target analytes. Target analytes include, but are not limited to, antigens, peptides, proteins, and other amino-acid containing moieties, biomarkers, RNA, DNA, oligonucleotides, including oligonucleotides containing DNA bases, RNA bases, both DNA and RNA bases, and synthetic bases, nucleic acid fragments, and lipids. Biomarkers that are expressed in tumor tissues, in the tumor microenvironment, and tissues representative of other disease states, are particularly important. Examples of such target biomarkers include, but are not limited to, tumor markers such as Sox10, S100, pan-cytokeratin, PAX5, PAX8; immune cell identifiers such as CD3, CD4, CD8, CD20, FoxP3, CD45RA, CD45LCA, CD68, CD163, CD11c, CD33, HLADR; activation markers such as Ki67, granzyme B; checkpoint-related markers such as TIM3, LAG3, PD1, PDL1, CTLA4, CD80, CD86, IDO-1, VISTA, CD47, CD26.

As discussed above, RNA target analytes can be identified using the methods described herein. The simulated H&E image of the sample, obtained as described herein, can be used to perform genetic analysis of a sample's DNA, and/or transcriptome analysis of a sample's RNA. The simulated H&E image can be used to identify regions of interest for analysis of RNA and/or DNA. For example, cancer regions can be identified within a sample based on the simulated H&E image, and these regions can be selected for specific types of analysis, such as the presence of one or more mutations, the assessment of tumor mutational burden, and other genetic analyses that seek to characterize tissue material of a specific type.

The assays described herein can be multiplexed to identify and optionally quantify multiple different target analytes. The number of analytes that can be identified and optionally quantified can be 5 or more (e.g., 10 or more, 20 or more, 30 or more, 50 or more, 100 or more, 200 or more, 300 or more, 500 or more, 700 or more, 1000 or more, 2000 or more, 3000 or more, 5000 or more, 10000 or more, or even more), and any number of analytes between 5 and 10000.

The methods described herein can be used to analyze a variety of different types of biological samples. In some embodiments, the biological sample can be fresh, frozen, or fixed. The biological sample can be of animal origin, such as from a human, mouse, rat, cow, pig, sheep, monkey, rabbit, fruit fly, frog, nematode or woodchuck. The biological sample can include formalin-fixed paraffin-embedded (FFPE) tissue sections, frozen tissue sections, fresh tissue, cells obtained from a subject (e.g., via fine-needle aspirate or other technique), cultured cells, biological tissue, biological fluid, a homogenate, or an unknown biological sample.

In certain embodiments, the biological sample can be immobilized on a surface. For example, the surface can be a slide, a plate, a well, a tube, a membrane, or a film. In some embodiments, the biological sample can be mounted on a slide. In certain embodiments, the biological sample can be fixed using a fixative, such as an aldehyde, an alcohol, an oxidizing agent, a mercurial, a picrate, HOPE fixative, or another fixative. The biological sample may alternatively, or in addition, be fixed using heat fixation. Fixation can also be achieved via immersion or perfusion.

In the discussion above, a single cycle of antigen retrieval is performed. More generally, however, any of the methods described herein can include multiple cycles of antigen retrieval (e.g., 2 or more, 3 or more, 4 or more, 5 or more, 7 or more, 10 or more, or even more). The number of cycles of antigen retrieval can generally be selected as appropriate for detection of particular target analytes. Antigen retrieval may employ various reagents, temperatures, times, and instruments. The sample may be subjected to reagents such as a 0.3% hydrogen peroxide solution to block endogenous peroxidase. Blocking buffers of various kinds may be used to reduce false detection of proteins, and biotin blockers may be used when biotin-based detection is employed.

The discussion above largely focuses on the use of hematoxylin analogs to stain a sample and generate a simulated H&E image. It should be noted, however, that eosin analogs can also be used with hematoxylin and with hematoxylin analogs in the methods described herein. One suitable eosin analog is indigo carmine, which functions as a counterstain. Indigo carmine is a fluorescent acidophilic stain that emits in deep red wavelengths. It can be after the sample has been imaged to create the simulated H&E view, using the same antigen retrieval techniques described herein.

Reagent Kits

Any of the reagents and compositions described herein can be packaged together in a reagent kit for processing a biological sample. The kits can be enclosed within a housing (e.g., a packaging material such as flexible plastic or paper, or a hard packaging such as a vial, bottle, tube, or other sealed and/or re-sealable package. The kits can include instructions for use, including instructions that describe any of the processing steps described herein.

Reagents that can be included in the kits can include, without limitation, hematoxylin, hematoxylin analogs, eosin, eosin analogs, chromogenic stains, fluorescent stains, fluorescent labels and reagents containing fluorescent species, antigen retrieval reagents, buffer reagents, dye fixatives, and alum.

Hardware and Software Systems

The methods described herein can be implemented in a variety of different analysis systems, including systems that perform some or all of the steps in semi-automated or fully automated fashion. One example of such a system 1200 is shown schematically in FIG. 12. System 1200 includes a storage unit 1202, a labeling station 1204, an imaging station 1206, and a translation apparatus 1210. Each of these components is connected to controller 1208, which includes one or more electronic processors that perform control functions associated with controller 1208, and can also perform any of the other analysis functions described herein.

Translation apparatus 1210 includes a slide handler 1212 that attaches to individual slides with samples in enclosed chambers to transport the slides between different locations in the system. An example of a slide with an enclosed chamber and a sample within the chamber is indicated as slide 1250 in FIG. 12. Slide handler 1212 can be implemented in a number of ways. In some embodiments, for example, slide handler 1212 is a grasper and includes one or more arms or fingers that exert pressure on surfaces of slide 1250 to lift and transport slide 1250. In certain embodiments, slide handler 1212 includes a member with one or more suction ports that uses reduced pressure to lift individual slides 1250. In certain embodiments, slide handler 1212 includes one or more members that are inserted under slides 1250 to lift the slides. In general, slide handler 1212 can permit both rotational displacements of slides 1250 about three orthogonal axes, and translations along three orthogonal axes.

Translation apparatus 1210 can also include a track or conveyor 1213 that carries individual slides 1250 or containers of slides between locations in system 1200. In some embodiments, track 1213 is a linear track that moves back and forth along a single direction between locations. In certain embodiments, track 1213 is a continuous track (e.g., circular, elliptical, or another continuous shape) that circulates among locations in the system.

During operation, controller 1208 can transmit appropriate control signals to translation apparatus 1210 to retrieve one or more slides 1250 from storage unit 1202, and to deposit one or more slides into storage unit 1202, as discussed above. Further, controller 1208 can transmit control signals to translation apparatus 1210 to activate labeling station to deliver fluids, reagents, and compositions to the chamber of slide 1250, and remove fluids, reagents, compositions (and components thereof) from the chamber of slide 1250). Labeling station 1204 includes a fluidic apparatus 1214 connected to one or more reservoirs 1218 and to one or more pumps and/or vacuum sources 1219. The fluidic apparatus 1214 includes one or more fluid conduits 1216 (e.g., syringes, tubes) that can selectively couple to ports in proximity to slide 1250. During operation of the system, controller 1208 transmits signals to translation apparatus 1210 to position slide 1250 within labeling station 1204, and transmits signals to the fluidic apparatus 1214 to cause one or more of the fluid conduits to deliver fluids, reagents, and compositions from reservoirs 1218 onto slide 1250, and fluids, reagents, and compositions (and components thereof) are removed from the slide, so that controller 1208 can implement any of the staining and labeling operations described herein in automated fashion. Under the control of controller 1208, labeling station 1204 can perform any of the sample preparation steps described herein.

Imaging station 1206 includes a radiation source 1220, an objective lens 1224, a beam splitter 1222, and an image detector 1226. Radiation source 1220 can include any one or more of a variety of different sources, including but not limited to LEDs, laser diodes, metal halide sources, incandescent sources, and fluorescent sources. Image detector 1226 can include one or more different detector types, including but not limited to CCD detectors and CMOS detectors. During operation of system 1200, to obtain an image of a sample within the chamber of slide 1250, controller 1208 activates translation apparatus 1210 to position slide 1250 within imaging station 1206. Controller 1208 then transmits control signals to the components of the imaging station, activating source 1220 to deliver illumination radiation to the sample which passes through beam splitter 1222 and objective lens 1224 and is incident on the sample. Emitted light from the sample passes through objective lens 1224, is reflected from beam splitter 1222, and is incident on image detector 1226, which measures an image of the emitted light.

Figure 12:
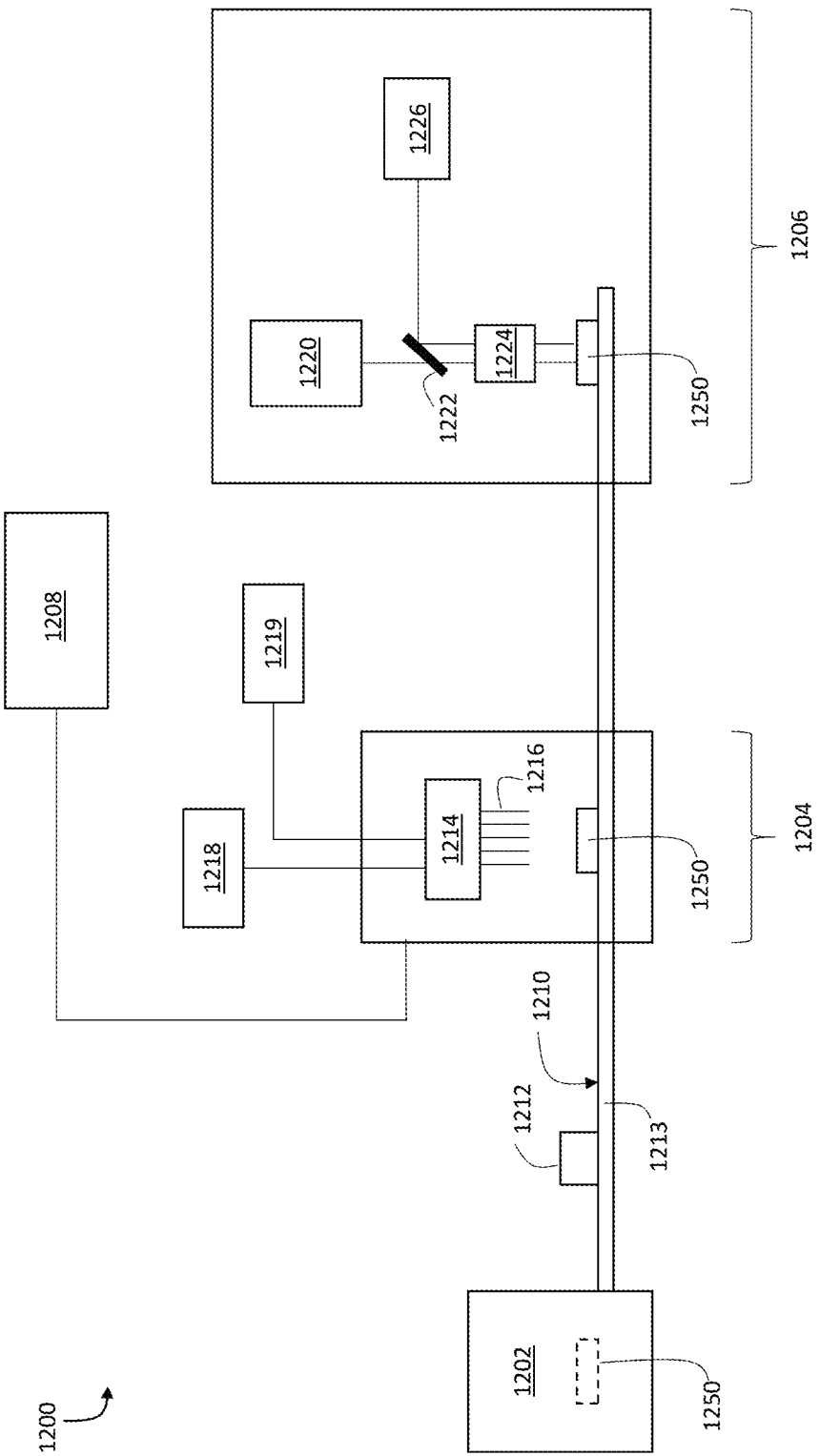
FIG. 12 is a schematic diagram of a system for analyzing a biological sample.

In FIG. 12, the imaging station is configured to obtain a fluorescence or reflected-light image of the sample. However, it should be appreciated that in some embodiments, detector 1226 can be positioned on an opposite side of slide 1250 from source 1220 to measure a transmitted-light image of the sample. In certain embodiments, imaging station 1206 includes multiple detectors for measuring both transmitted- and reflected- or emitted-light (e.g., fluorescence) images of the sample. Under the control of controller 1208, imaging station 1206 can obtain any of the different types of images corresponds to any of the different types of stains, probes, and labeling agents described herein.

As discussed previously, each of the steps in sample analysis consumes a certain amount of time, and improved efficiency can be obtained by translating multiple slides 1250 among multiple locations in system 1200, and performing multiple operations. For example, during analysis of multiple slides 1250, a first slide containing a first sample in a chamber can be positioned at the labeling station, and the fluidic apparatus can deliver one or more probes to the sample and incubate the sample with the delivered probes. At the same time, a second slide containing a second sample in a chamber can be positioned at the imaging station to obtain one or more images of stains or labeling agents in the sample. A third slide containing a third sample in a chamber can be positioned at the labeling station, where controller 1208 activates the one or more pumps and/or vacuum sources to remove fluids, reagents, and/or compositions (and components thereof) from the chamber of the third slide. A fourth slide containing a fourth sample in a chamber can be positioned at the labeling station, where controller 1208 activates the fluidic apparatus 1214 to deliver a composition that includes one or more primary antibodies into the chamber, and incubates the fourth sample with the antibody composition. Other slides 1250 can also be processed—undergoing any of the operations discussed herein—at the same time.

As each slide reaches the end of a set of one or more steps in a preparation or analysis workflow, the slide is transported by translation apparatus 1210 to a different location in the system—to a different station, or to a different location within the same station, for example. In this manner, system 1200 can simultaneously analyze multiple samples, ensuring that the duty cycles of the components of system 1200 remain relatively high, increasing overall throughput of the system for multiple samples relative to simple linear processing of individual samples.

Figure 13:
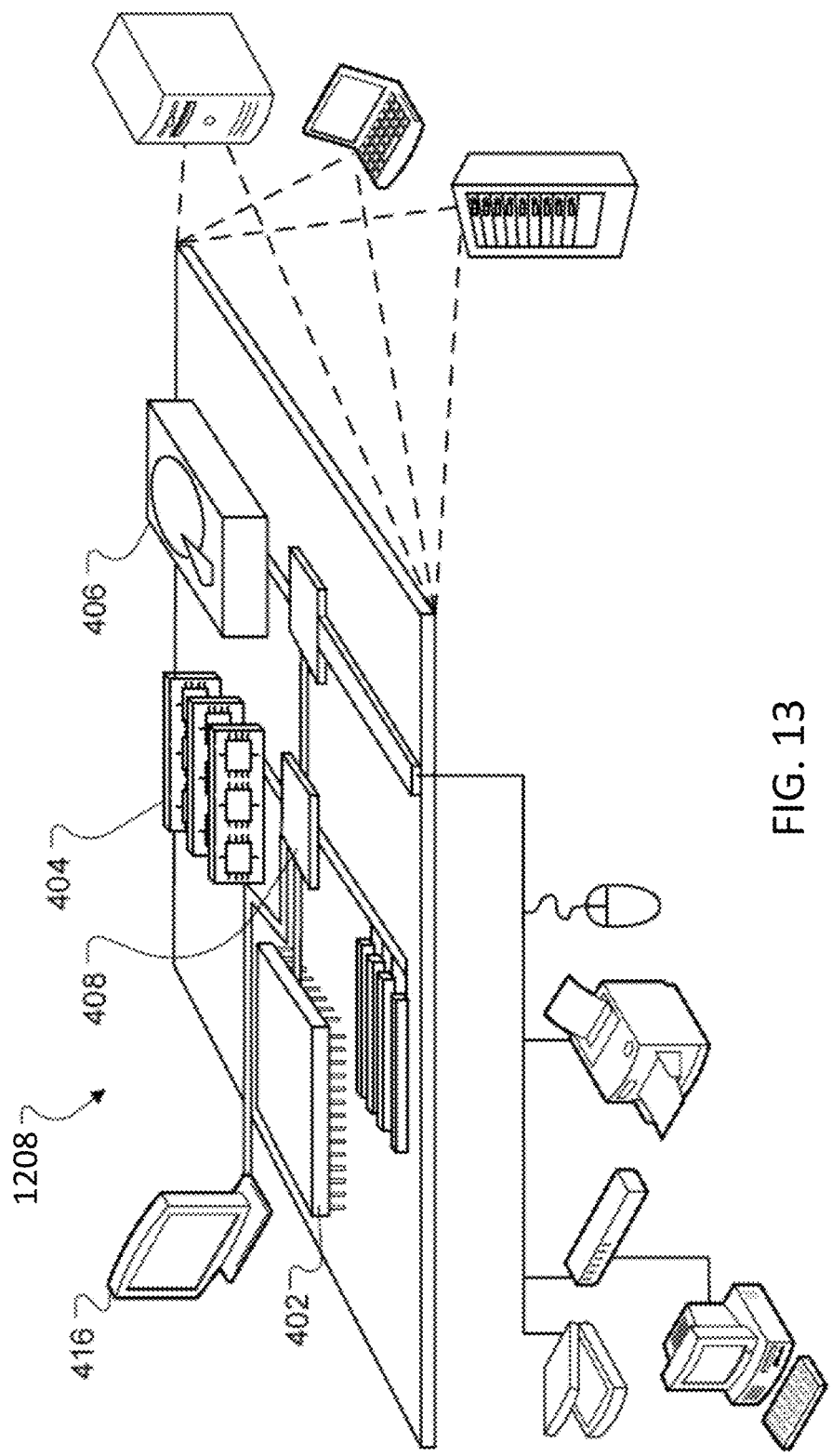
FIG. 13 is a schematic diagram of a controller.

FIG. 13 shows an example of controller 1208, which may be used with the systems and methods disclosed herein. Controller 1208 can include one or more processors 402, memory 404, a storage device 406 and interfaces 408 for interconnection. The processor(s) 402 can process instructions for execution within the controller, including instructions stored in the memory 404 or on the storage device 406. For example, the instructions can instruct the processor 402 to perform any of the analysis and control steps disclosed herein.

The memory 404 can store executable instructions for processor 402, information about parameters of the system such as excitation and detection wavelengths, and measured spectral image information. The storage device 406 can be a computer-readable medium, such as a floppy disk device, a hard disk device, an optical disk device, or a tape device, a flash memory or other similar solid state memory device, or an array of devices, including devices in a storage area network or other configurations. The storage device 406 can store instructions that can be executed by processor 402 described above, and any of the other information that can be stored by memory 404.

In some embodiments, controller 1208 can include a graphics processing unit to display graphical information (e.g., using a GUI or text interface) on an external input/output device, such as display 416. The graphical information can be displayed by a display device (e.g., a CRT (cathode ray tube) or LCD (liquid crystal display) monitor) for displaying any of the information, disclosed herein. For example, the displayed information can include simulated H&E images, multi spectral images, annotations and other information entered by a user. A user can use input devices (e.g., keyboard, pointing device, touch screen, speech recognition device) to provide input to controller 1208.

A user of system 1200 can provide a variety of different types of instructions and information to controller 1208 via input devices. The instructions and information can include, for example, information about any of the parameters (e.g., stains, labels, probes, reagents, conditions) associated with any of the staining and labeling protocols described herein, calibration information for quantitative analysis of sample images, and instructions following manual analysis of sample images by a technician. Controller 1208 can use any of these various types of information to perform the methods and functions described herein. It should also be noted that any of these types of information can be stored (e.g., in storage device 406) and recalled when needed by controller 1208.

The methods disclosed herein can be implemented by controller 1208 by executing instructions in one or more computer programs that are executable and/or interpretable by the controller 1208. These computer programs (also known as programs, software, software applications or code) include machine instructions for a programmable processor, and can be implemented in a high-level procedural and/or object-oriented programming language, and/or in assembly/machine language. For example, computer programs can contain the instructions that can be stored in memory 404, in storage unit 406, and/or on a tangible, computer-readable medium, and executed by processor 402 as described above. As used herein, the term "computer-readable medium" refers to any computer program product, apparatus and/or device (e.g., magnetic discs, optical disks, memory, Programmable Logic Devices (PLDs), ASICs, and electronic circuitry) used to provide machine instructions and/or data to a programmable processor, including a machine-readable medium that receives machine instructions.

EXAMPLES

Example 1: Curcumin and Eosin Staining

This experiment makes use of curcumin ((E,E)-1,7-bis (4-hydroxy-3-methoxyphenyl)-1,6-heptadiene-3,5-dione, CAS Number 458-37-7, Sigma-Aldrich) and alum (potassium aluminum sulfate dodecahydrate, CAS Number 7784-24-9, Sigma-Aldrich). An aqueous curcumin-alum solution was made by creating a saturated curcumin solution in double-distilled, autoclaved water to which was added 0.5% alum by weight. This solution was then brought to 80° C. for 1 hour. The curcumin-alum solution can be prepared up to 2 months in advance of its use.

The experiment also makes use of eosin Y disodium salt (CAS Number 17372-87-1, Sigma-Aldrich). This was used to prepare an acidic solution of eosin in alcohol. It was a very dilute solution compared with what is typical for conventional, bright-field histological staining with eosin. The solution was made from histology grade alcohol (Reagent Grade, Histology Grade, VWR 89370-084) containing a small amount of eosin Y salt, 0.001% by weight or less. Experiments have indicated that concentrations of 0.001% or less (e.g., 0.0005% or less, 0.0001% or less, 0.00005% or less, or even less) can still be used for sample staining to generate a simulated H&E image. A slightly acidic pH was obtained by adding a small amount of glacial acetic acid, 0.005% by volume.

The eosin Y solution is typically prepared immediately before use but can be diluted to a working solution of 0.0001% up to 2 months in advance. Acetic acid was added immediately before use. Diluted eosin Y solution to which acetic acid was added was discarded after use.

Three FFPE human lung cancer tissue sections were cut to a thickness of 5 microns, mounted to positively-charged 25 mm×75 mm microscope slides (Superfrost, Fisher Scientific), baked at 65° C. for 3 hours, and deparaffinized and rehydrated with 3 10-minute xylene baths (Histology Grade, VWR 89370-088), one ten-minute 100% alcohol bath (Reagent Grade, Histology Grade, VWR 89370-084), one 5-minute 95% alcohol bath (Reagent Grade, Histology Grade, VWR 89370-082), one 5-minute 70% alcohol bath (Reagent Grade, Histology Grade, VWR 89370-078), and one 2-minute autoclaved double-distilled H$_2$O bath.

They were then stained for 30 minutes with the curcumin-alum solution. After this, they were dried with one 5-minute in a 70% alcohol bath and one 5-minute in a 95% alcohol bath, then stained with the eosin solution for 5 minutes. They were then dehydrated in two ten-minute xylene baths, a drop of Cytoseal 60 (Richard-Allan Scientific) mounting medium was applied, and a #1.5 coverslip was attached. Then the samples were imaged using a Vectra Polaris® (Akoya Biosciences) imaging system using a whole-slide fluorescent imaging protocol with 8 imaging bands—DAPI, Opal 480, Opal 520, Opal 570, Opal 620, Opal 690, Opal 780, and Sample AF.

The coverslip was removed using xylene, the sample was washed with two ten-minute xylene baths to ensure no mounting medium remained, and the sample was rehydrated via one ten-minute 100% alcohol bath, one 5-minute 95% alcohol bath, one 5-minute 70% alcohol bath, and one 2-minute autoclaved double-distilled H$_2$O bath.

The samples were then subjected to antigen retrieval with microwave treatment. The samples were submerged in 250 mL 1× AR9 Buffer (PerkinElmer AR900250ML 10× stock diluted in autoclaved double-distilled H$_2$O) and placed in a Panasonic NN-SA651S microwave oven for 93 seconds at 100% power (default power setting) followed immediately by 15 minutes at 20% power (power setting "2").

Following this, they were cooled to room temperature and prepared with the Opal® MOTiF Lung Cancer kit (Akoya Biosciences, P/N OP-000001) in accordance with the manufacturer's instructions for that kit, using a Leica Bond autostainer. Because dewaxing and the antigen retrieval had been performed already, these steps were omitted, the slides were added to the machine in tris-buffered saline (TBS Buffer, 20× liquid, VWR J640-1L, diluted in autoclaved double-distilled H$_2$O), and the "frozen slide delay" "Preparation" was selected. When staining was complete, they were imaged with the Vectra Polaris® system using a MOTiF FL scanning protocol.

Figure 4B:
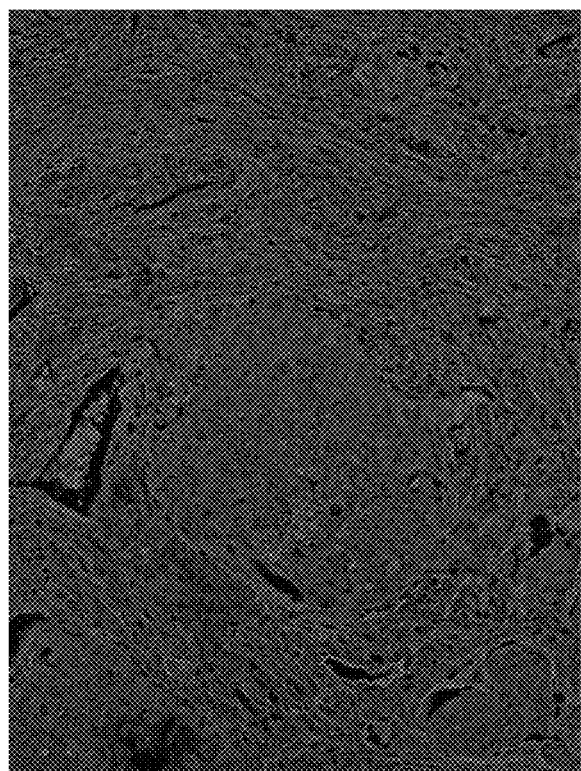
FIG. 4B is an image showing a fluorescent signal corresponding to eosin in the lung cancer tissue sample.
Figure 4A:
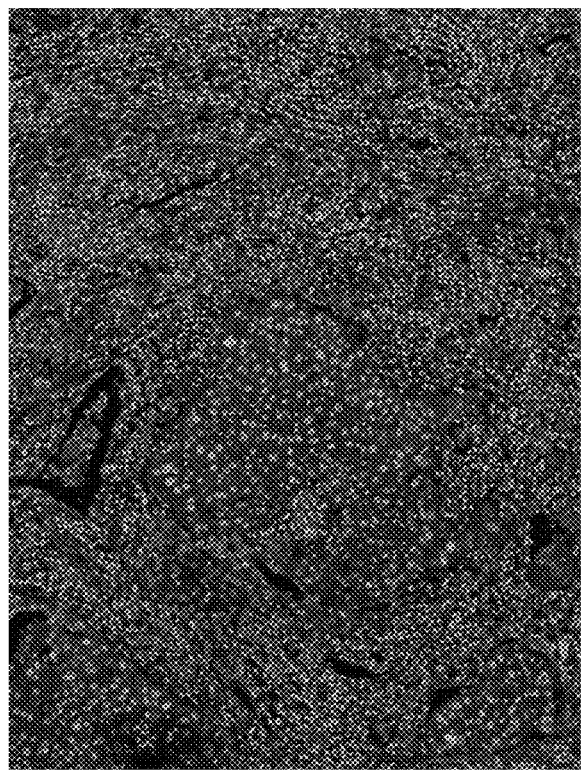
FIG. 4A is an image showing a fluorescent signal corresponding to curcumin in a lung cancer tissue sample.
Figure 4C:
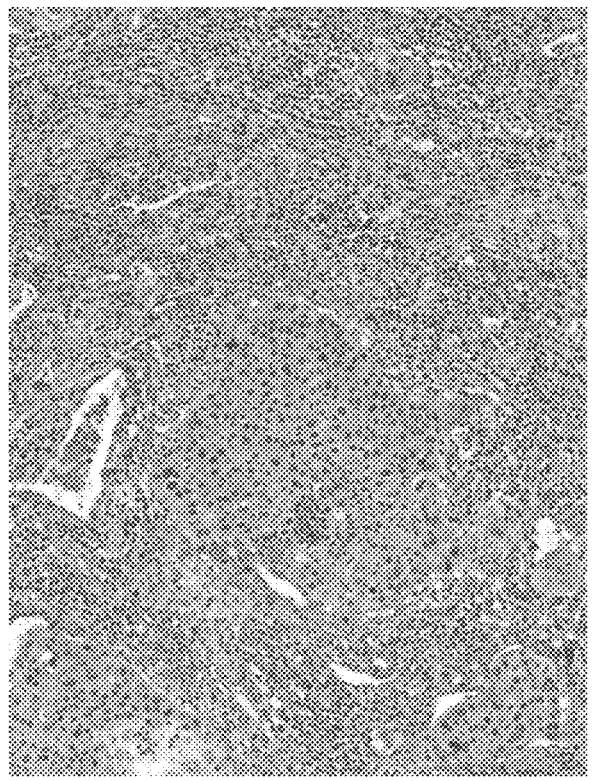
FIG. 4C is a simulated H&E image generated for the lung cancer tissue sample.
Figure 4D:
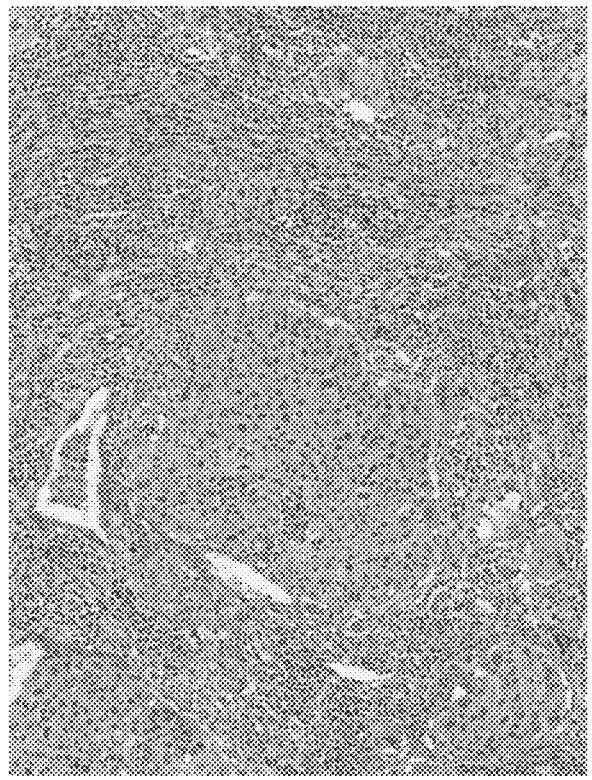
FIG. 4D is a conventional H&E image measured for the lung cancer tissue sample.
Figure 5A:
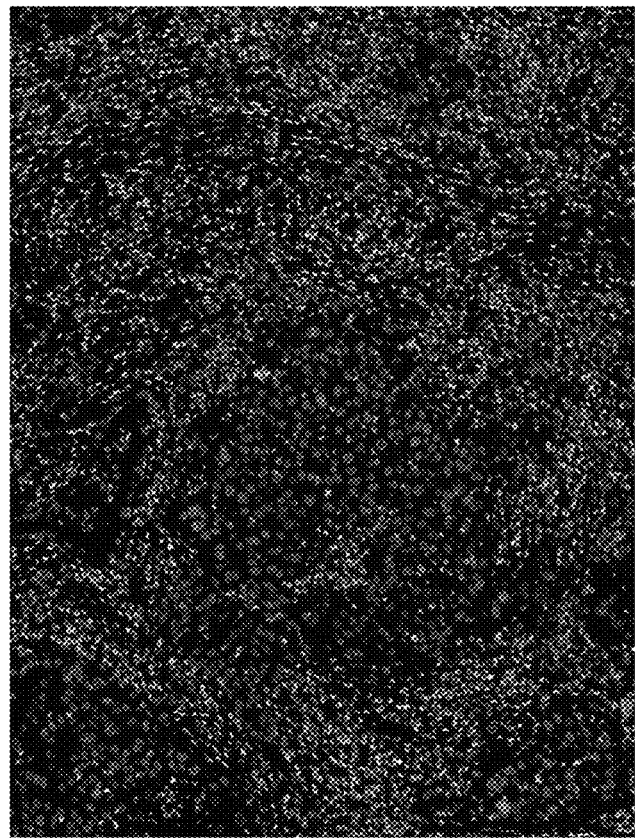
FIGS. 5A-5G are images showing immunohistochemical stains (e.g., immunofluorescent labels) that selectively target DNA (DAPI) and markers pan-cytokeratin, CD68, CD8, PD-1, PDL-1 and FoxP3, from the same tissue section used to generate the image in FIG. 4C.
Figure 5B:
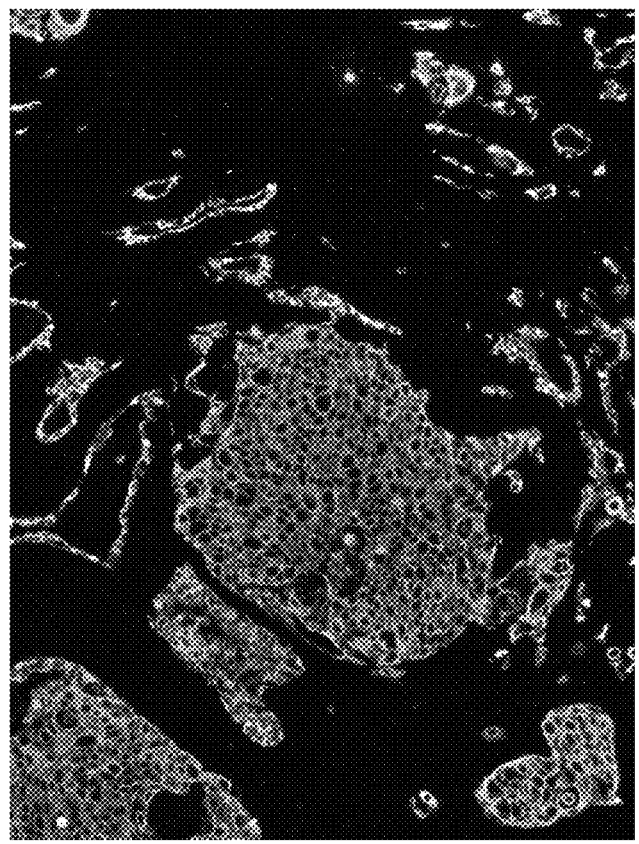
Figure 5D:
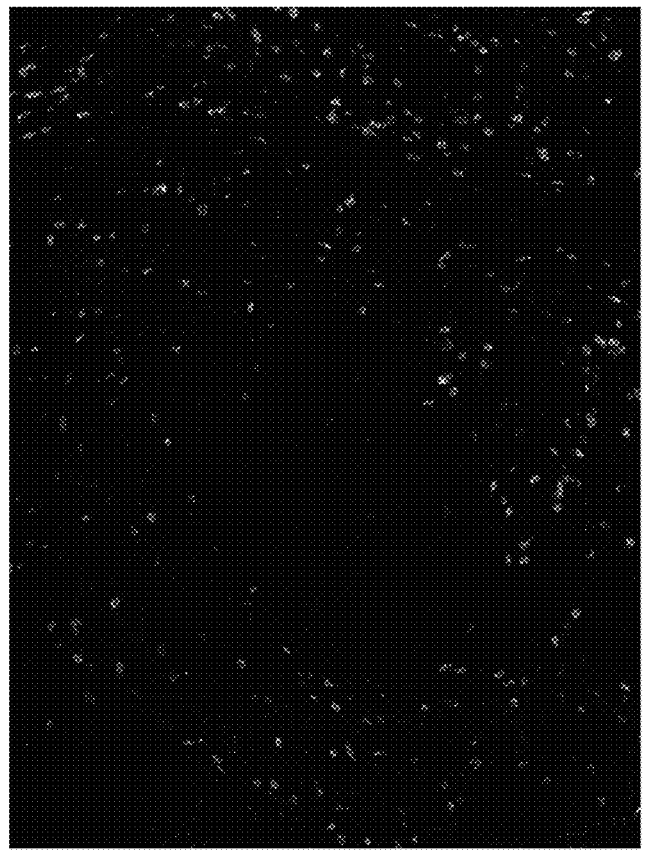
Figure 5C:
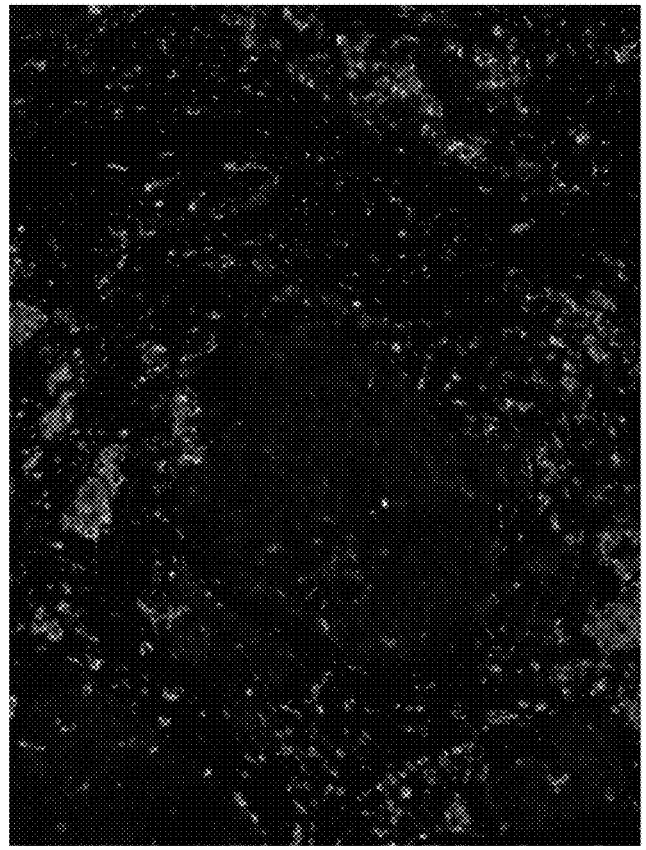
Figure 5F:
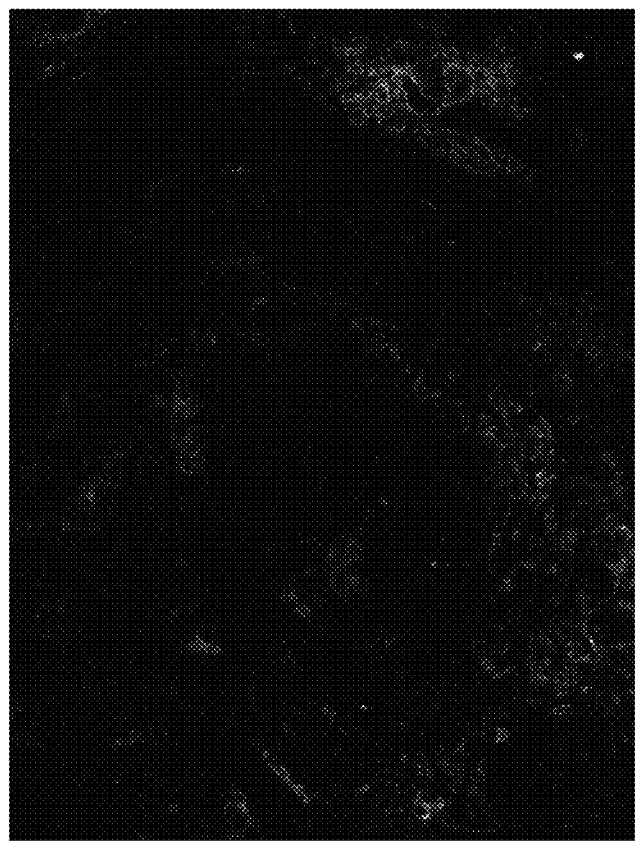
Figure 5E:
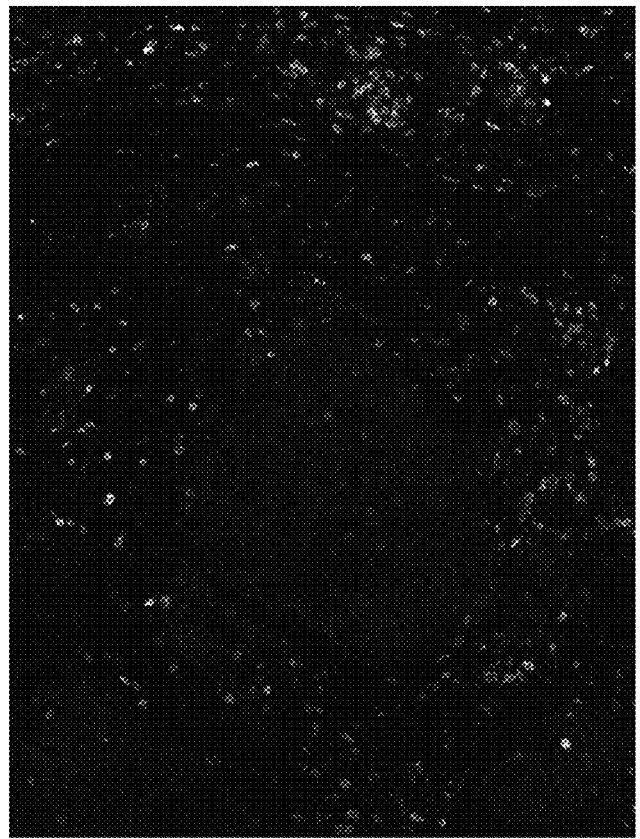
Figure 5G:
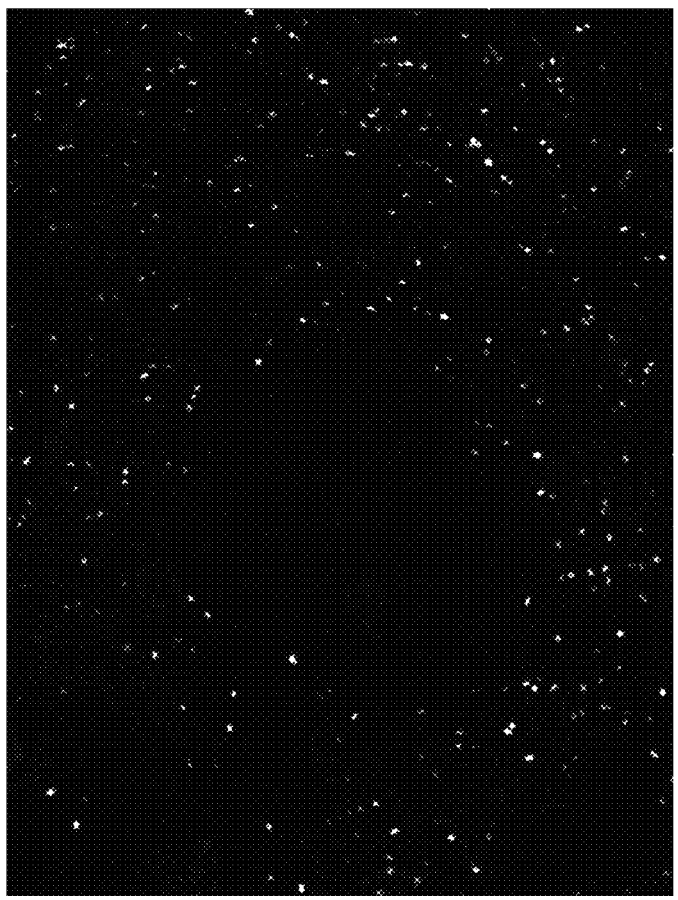
Figure 6B:
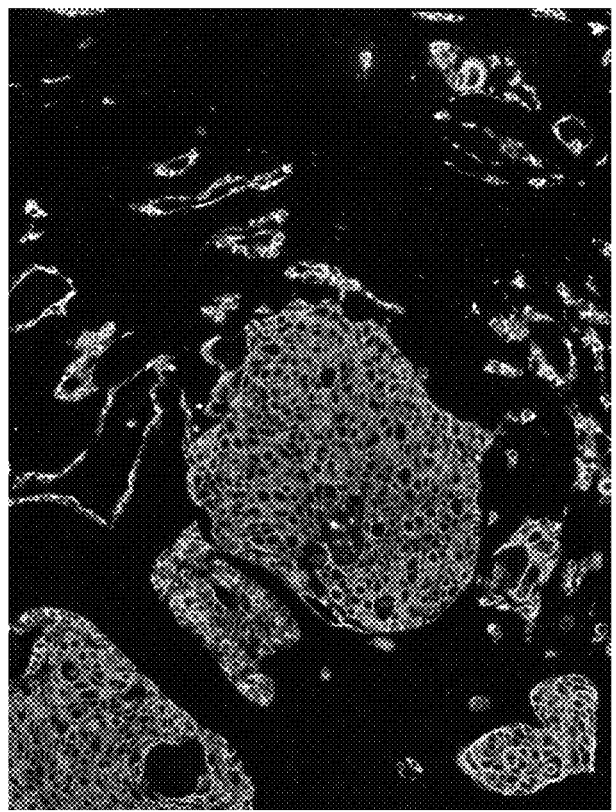
FIGS. 6A-6G are images showing immunohistochemical stains (e.g., immunofluorescent labels) that selectively target DNA (DAPI) and markers pan-cytokeratin, CD68, CD8, PD-1, PDL-1 and FoxP3, from a different tissue section cut from the lung cancer tissue sample as the tissue section of FIGS. 5A-5G.
Figure 6A:
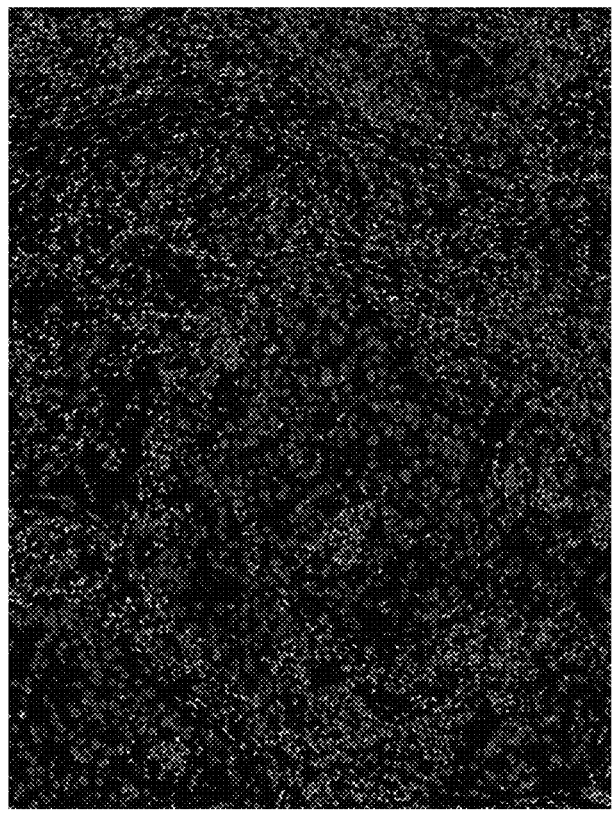
Figure 6D:
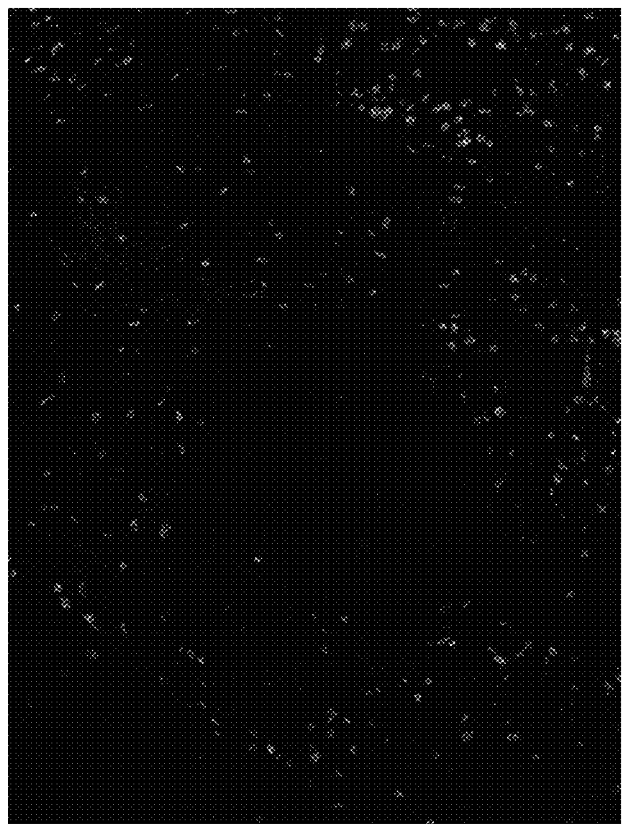
Figure 6C:
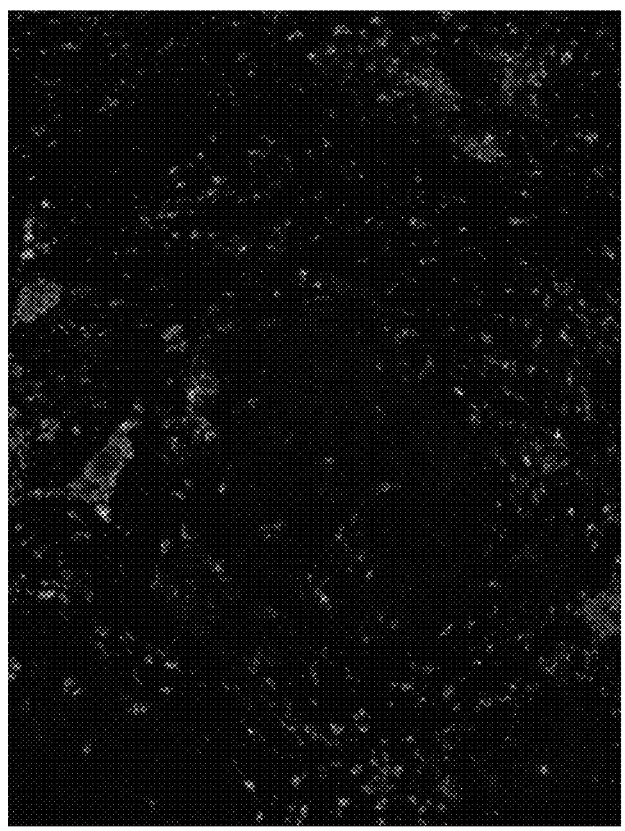
Figure 6F:
Figure 6E:
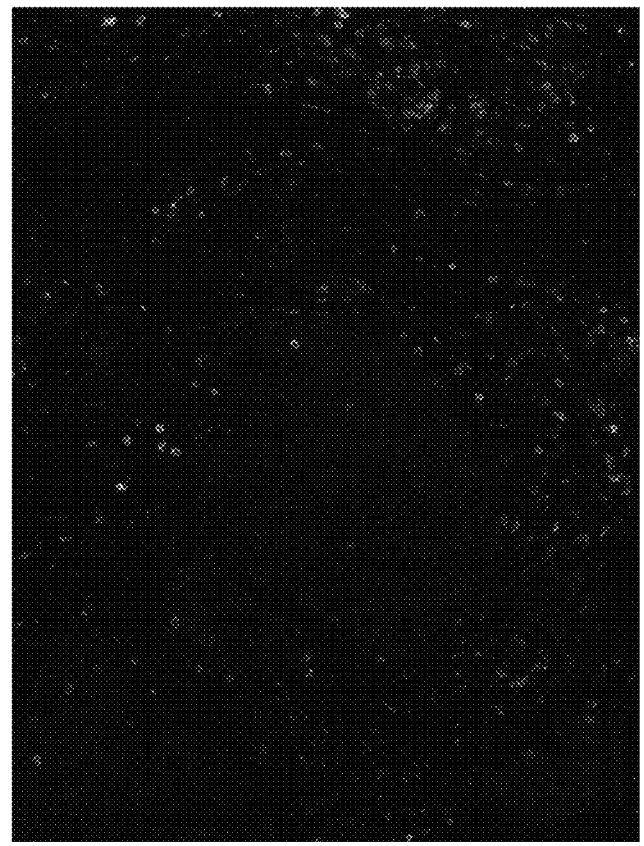
Figure 6G:
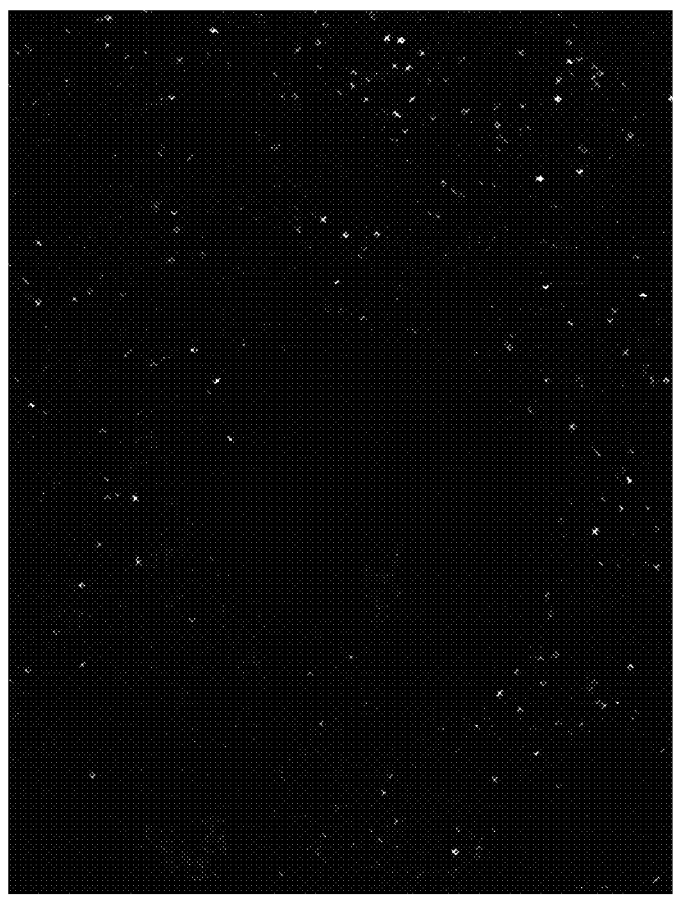

FIGS. 4A and 4B show measured fluorescent signals corresponding to curcumin and eosin, respectively, in one of the tissue samples. FIG. 4C shows the simulated H&E image generated for the sample from image information contained in FIGS. 4A and 4B, while FIG. 4D shows a conventional H&E image measured from another tissue section stained with a conventional H&E protocol. Close qualitative agreement between the images is observed.

FIGS. 5A-5G show measured fluorescence signals obtained following antigen retrieval and staining of the same tissue sample shown in FIGS. 4A and 4B with the Opal® MOTiF Lung Cancer kit. The images correspond to DAPI and fluorescent labels linked to markers pan-cytokeratin, CD68, CD8, PD-1, PDL-1, and FoxP3, respectively. FIGS. 6A-6G show measured fluorescence signals obtained from a different tissue section that was not stained with curcumin or eosin, but was instead directly stained with the Opal® MOTiF Lung Cancer kit. The images correspond to DAPI and fluorescent labels linked to markers pan-cytokeratin, CD68, CD8, PD-1, PDL-1, and FoxP3, respectively. As is evident from a comparison of the figures, images corresponding to the same markers appear qualitatively very similar, indicating that the initial staining with curcumin and eosin did not strongly affect the immunoassay.

Figure 7:
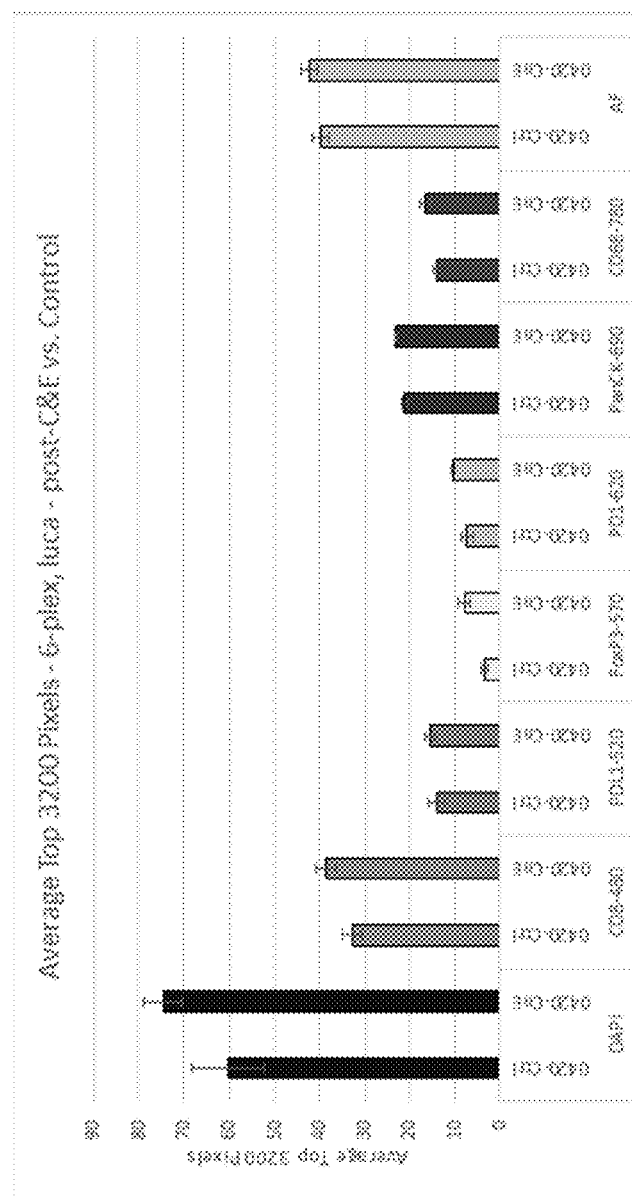
FIG. 7 is a graph showing expression levels of signals corresponding to DNA and the various markers for the tissue sections in FIGS. 5A-5G and FIGS. 6A-6G.

Expression levels of the various markers are shown on the graph of FIG. 7, and are quantitatively similar to one another.

Example 2: Carmine and Eosin Staining

This experiment uses carmine-alum and eosin Y-alum solution. Stock solutions were made as follows.

Starting with 250 mL deionized distilled water on a stirring hot plate, 1.25 g $KAI(SO_4)_2$ (Sigma, Cat #A6435-100G) was added. Temperature was increased to 30° C. When the alum was dissolved, 0.25 g carmine powder (Sigma, Cat #C1022-5G) was added, and the solution was heated to 80° C. Stirring was continued at 80° C. for 10 minutes. The solution was removed from hot plate and cooled to room temperature, then filtered and stored in a glass bottle.

5 g $KAI(SO_4)_2$ (Sigma, Cat #A6435-100G) was added to 500 mL deionized distilled water, and placed in an 80° C. oven, stirring intermittently until the alum was dissolved. When the solution was at 80° C., 0.5 g eosin Y disodium salt (Sigma-Aldrich, Cat #E4382-25G) was added. The solution remained in the oven for 30 minutes, stirring intermittently. The solution was removed from the oven and cooled to room temperature, then filtered through Grade 1 Whatman paper (Sigma-Aldrich, SKU #WHA1001055) and stored in a glass bottle.

In this experiment, 3 mL of carmine-alum 1× stock and 7 mL of eosin Y-alum 1× stock were mixed to form a working solution of carmine and eosin used to stain samples. Sections were cut from an FFPE lung cancer sample block, with a thickness of 5 microns. Each cut section was put on a VWR Superfrost slide, and dewaxed by baking at 65° C. for 3 hours, and deparaffinized and rehydrated with 3 10-minute xylene baths (Histology Grade, VWR 89370-088), one ten-minute 100% alcohol bath (Reagent Grade, Histology Grade, VWR 89370-084), one 5-minute 95% alcohol bath (Reagent Grade, Histology Grade, VWR 89370-082), one 5-minute 70% alcohol bath (Reagent Grade, Histology Grade, VWR 89370-078), and one 2-minute autoclaved double-distilled $H_2O$ bath.

Samples were covered by 500 µL of the working solution of carmine and eosin for 5 minutes, then rinsed in autoclaved double-deionized $H_2O$, a 5-minute 70% alcohol bath, a 5-minute 95% alcohol bath, and a 10-second 70% alcohol bath to remove excess eosin, then returned to an autoclaved double-deionized $H_2O$ bath, after which 2 drops of H&E Mount™ (Innovex biosciences, Richmond CA) were applied and a #1.5 coverslip was affixed. Alternatively, samples could have been dehydrated following carmine and eosin staining in a 5-minute 70% alcohol bath, a 5-minute 95% alcohol bath, a 5-minute 100% alcohol bath, two 10-minute xylene baths (VWR reagents listed previously) and mounted with a drop of Cytoseal 60 (Richard-Allen Scientific) for imaging and long-term storage.

The samples were imaged in a Vectra Polaris® imaging system using a whole-slide fluorescent imaging protocol with 8 imaging bands—DAPI, Opal 480, Opal 520, Opal 570, Opal 620, Opal 690, Opal 780, and Sample AF. One sample was also imaged with the same apparatus, using a brightfield imaging protocol.

Other baked samples were used as controls and were neither deparaffinized and rehydrated, stained with the carmine and eosin solution, nor were they imaged at this point in the experiment.

The samples that had been stained and imaged had their coverslips removed using autoclaved double-distilled water and were then washed with autoclaved double-distilled $H_2O$ for 5 minutes to remove any residual mounting medium.

The carmine and eosin-treated samples were then subjected to antigen retrieval using microwave treatment. The samples were submerged in 250 mL 1× AR9 Buffer (PerkinElmer AR900250ML 10× stock diluted in autoclaved double-distilled $H_2O$) solution and placed in a Panasonic NN-SA651S microwave oven for 93 seconds at 100% power (default power setting) followed immediately by 15 minutes at 20% power (power setting "2").

Samples were imaged using the same fluorescent imaging protocol to assess the residual effect of the carmine and eosin stains (for the samples receiving this treatment), compared with the signal levels in the unstained controls.

Following this, they were prepared with the Opal® MOTiF Lung Cancer kit in accordance with the manufacturer's instructions for that kit, using a Leica Bond autostainer. Once again, because dewaxing had been performed already for the carmine and eosin slides, these steps were omitted and these slides were subjected to "frozen slide delay" "Preparation" step in the Bond instrument. Control slides, which had been baked at 65° C. for 3 hours but not deparaffinized or rehydrated, were subjected to "Dewax" "Preparation" on the Bond Rx. Downstream of these differing "Preparation" treatments all slides were subjected to the same HIER and staining protocols using the same reagent preparations. Staining protocol starting times differed across control versus carmine and eosin-treated slides by roughly 40 minutes due to the extra time allotted for "Dewax" "Preparation" steps. Samples were then imaged with a Vectra Polaris® using a MOTiF FL scanning protocol.

The mIF signals were measured for all samples, and the levels were compared for the samples which had been stained with carmine and eosin at the outset, against the levels for the control sample that had not received that staining.

Figure 9A:
FIG. 9A is an image of a measured fluorescent signal associated with carmine-alum in a lung cancer tissue section.
Figure 9B:
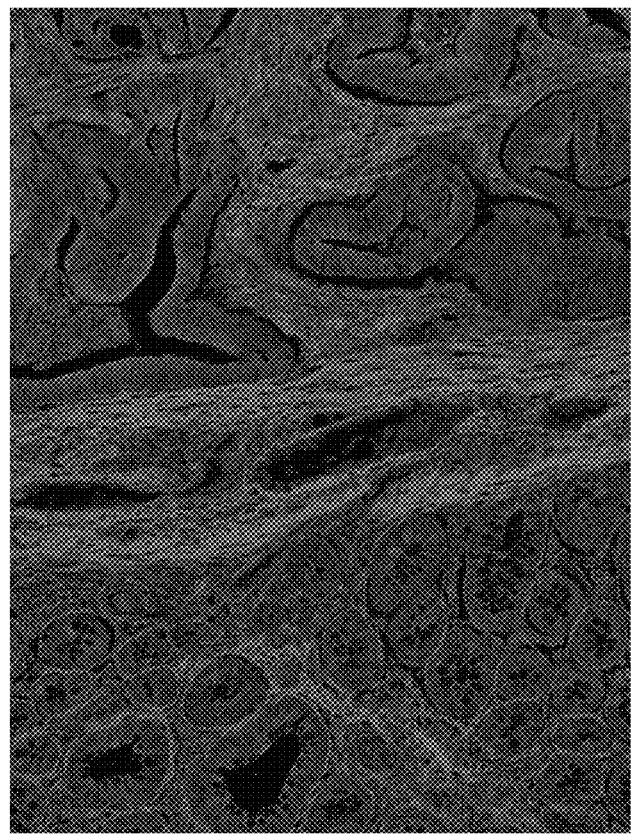
FIG. 9B is an image of a measured fluorescent signal associated with eosin Y-alum in the lung cancer tissue section of FIG. 9A.
Figure 9D:
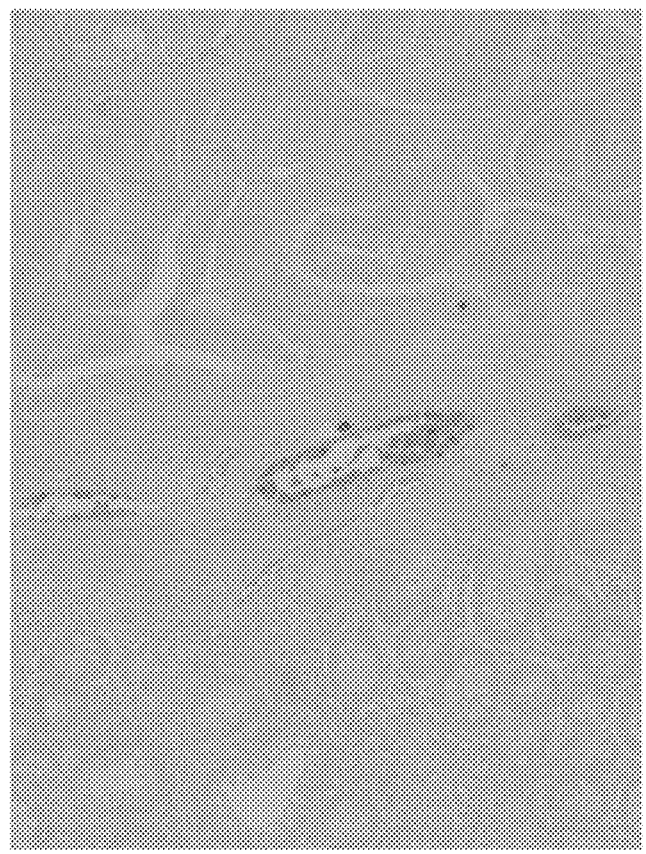
FIG. 9D is a transmitted-light image lung cancer tissue section of FIG. 9A following staining with carmine-alum and eosin Y.
Figure 9C:
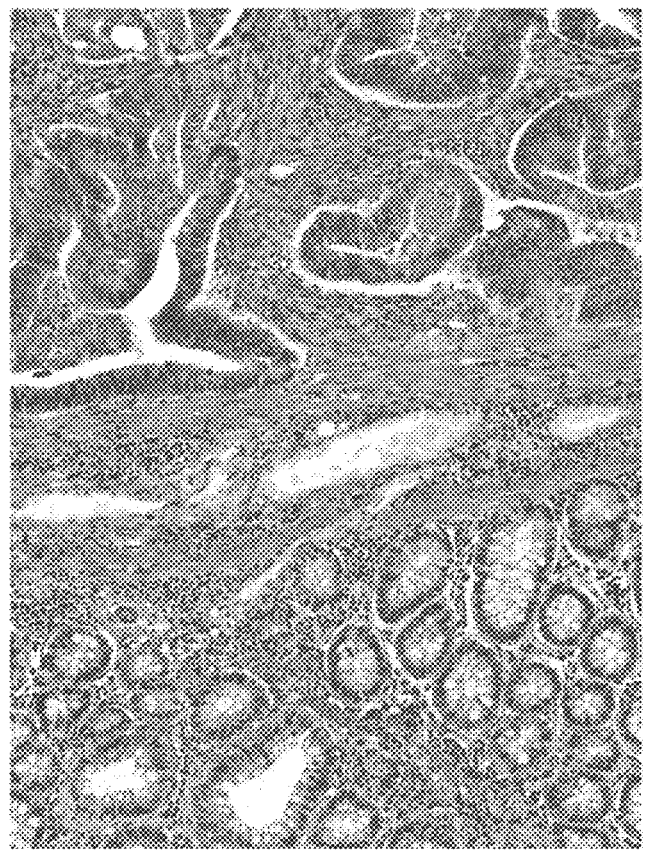
FIG. 9C is a simulated H&E image generated from the measured fluorescent signals in FIGS. 9A and 9B.
Figure 9E:
FIG. 9E is a simulated H&E image of the lung cancer tissue section of FIG. 9A generated from the fluorescent signals associated with carmine-alum and eosin Y and the transmitted light image of FIG. 9D.

FIGS. 9A and 9B show measured fluorescence signals from carmine and eosin stains, respectively, and FIG. 9C shows the simulated H&E image obtained from the image information in FIGS. 9A and 9B. FIG. 9D shows a transmitted light image from the same tissue section, and FIG. 9E shows a simulated H&E image generated from the fluorescent signals associated with both carmine and eosin stains (FIGS. 9A and 9B), and the transmitted light image (FIG. 9D). The images in FIGS. 9C and 9E are similar, with the image in FIG. 9E showing greater detail due to the inclusion of the transmitted light information.

Figure 9F:
FIG. 9F is a conventional H&E image of another lung cancer tissue section obtained from the same tissue block as the lung cancer tissue section of FIG. 9A, and stained with a conventional H&E protocol.

FIG. 9F is a conventional H&E image obtained from another tissue section stained according to a conventional H&E protocol. FIGS. 9E and 9F show a high degree of qualitative similarity.

Figure 10A:
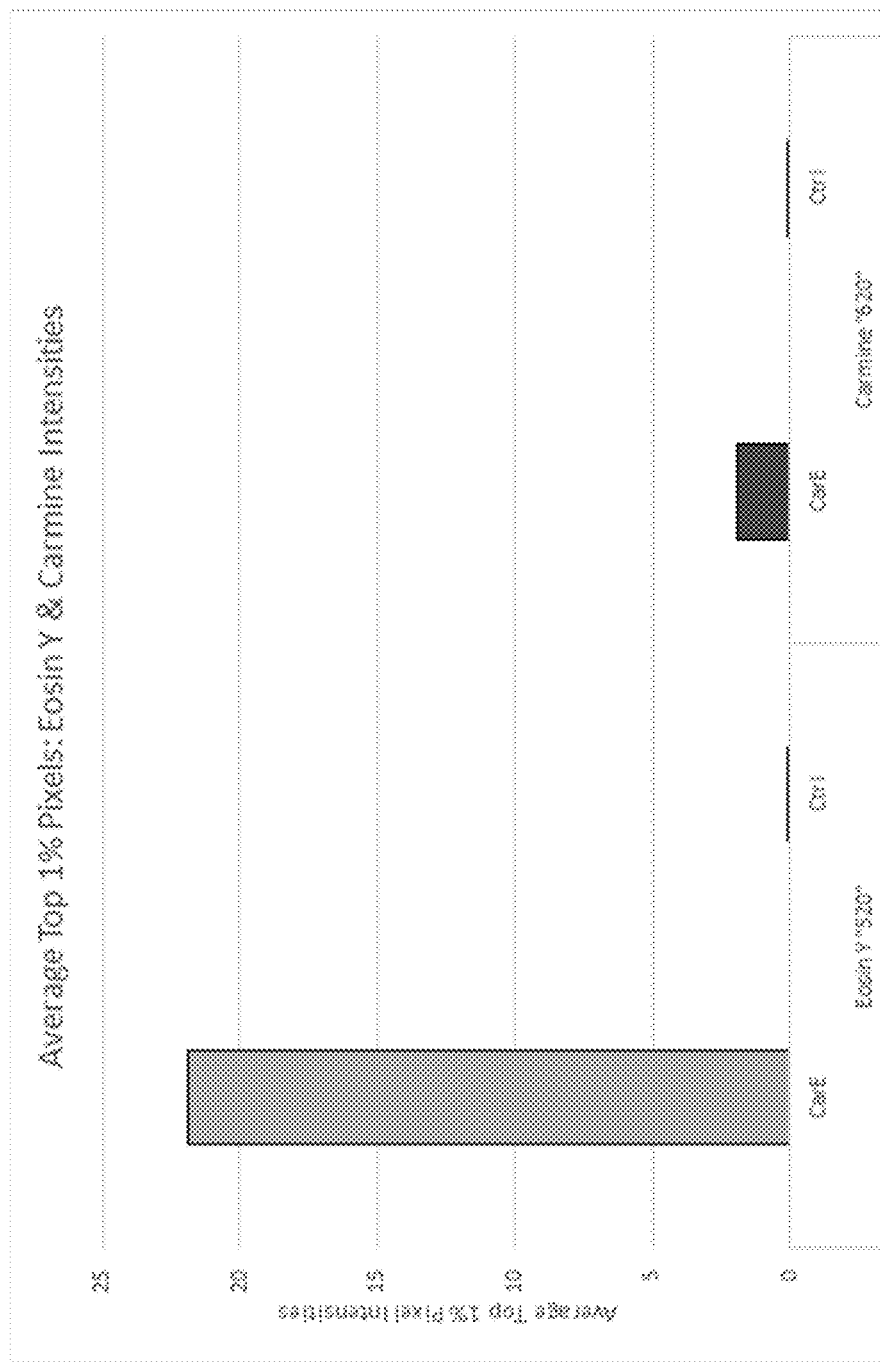
FIG. 10A is a graph showing measured signal intensities for carmine and eosin in a tissue sample.
Figure 10B:
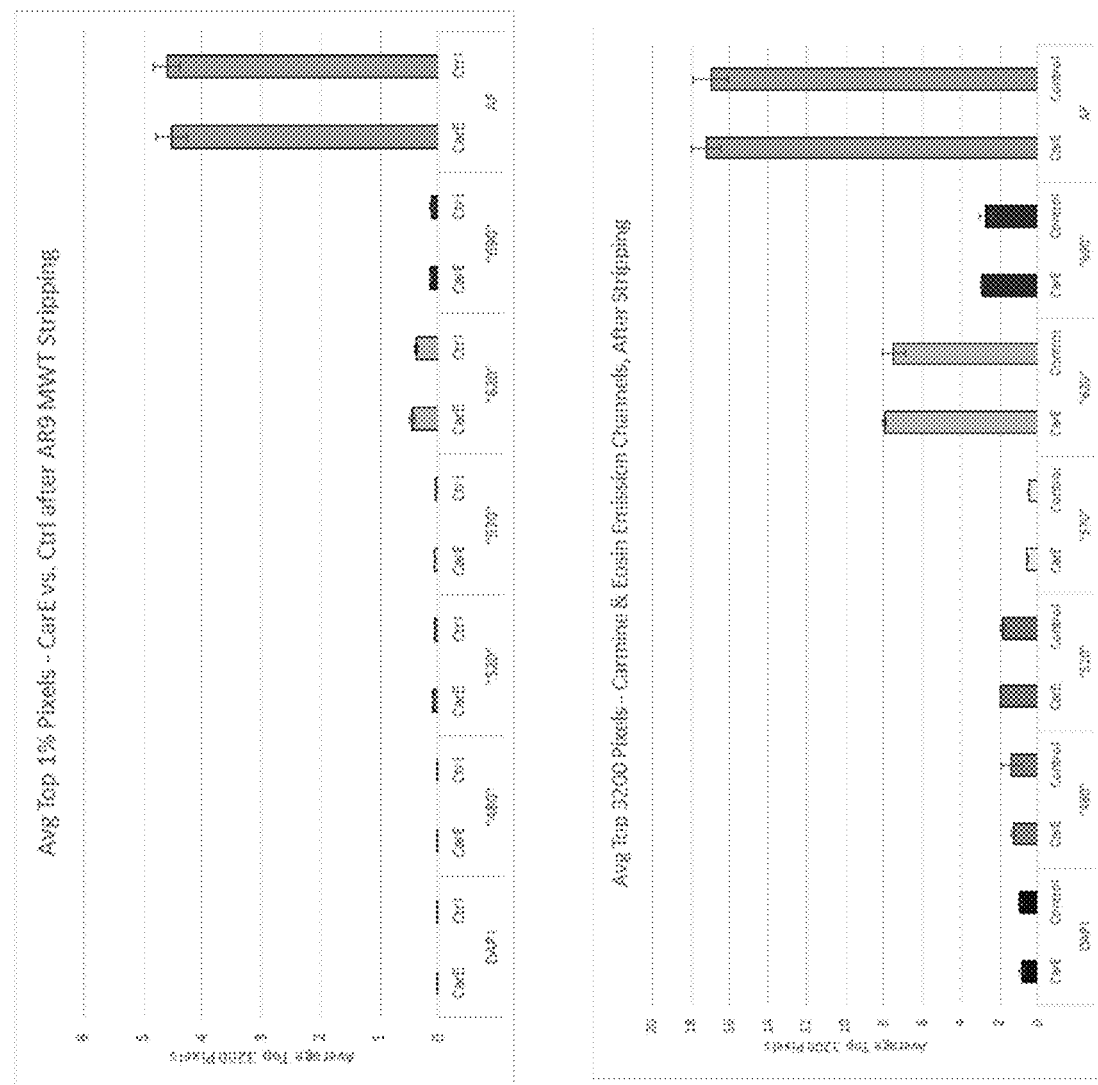
FIG. 10B is a graph showing measured signal intensities for carmine in the tissue section of FIG. 9A after an antigen retrieval step.
Figure 11:
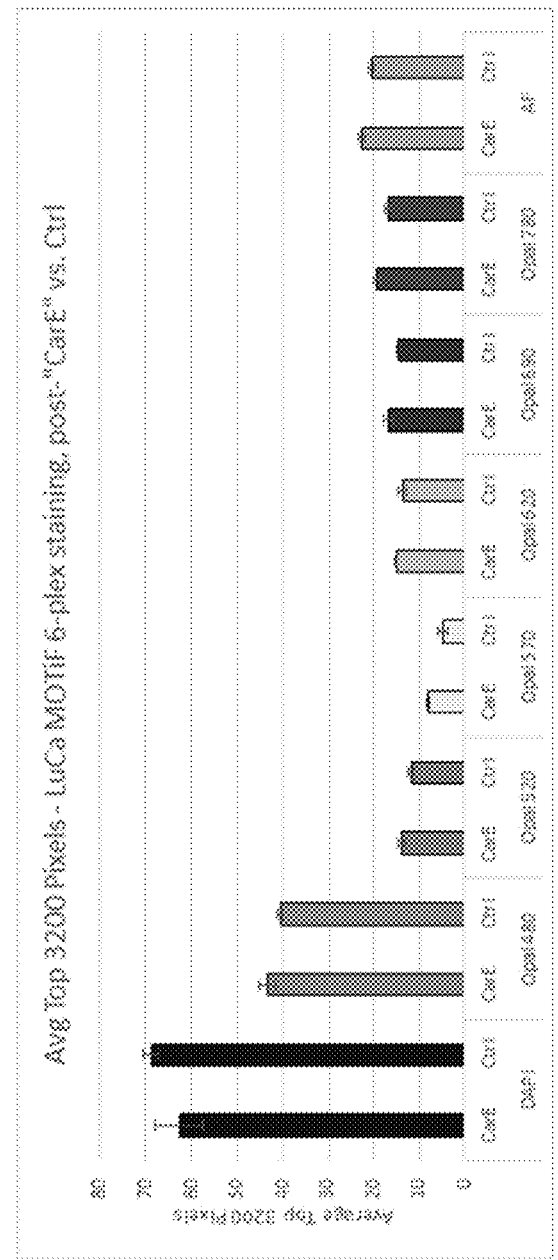
FIG. 11 is a graph showing measured signal intensities for carmine in the tissue section of FIG. 9A after staining with a panel of antibody-linked fluorescent labels.

FIG. 10A shows measured signal intensities for carmine and eosin in the carmine and eosin spectral channels, and FIG. 10B shows measured signal intensities for carmine following antigen retrieval in various spectral channels corresponding to the 8 imaging bands described above, compared to a control sample. The measured intensities indicate that residual fluorescence signals due to carmine are very small. FIG. 11 shows measured signal intensities for carmine following staining with the fluorescent labels of the Opal® MOTiF Lung Cancer kit, and imaging using filters tuned to the emission bands of the fluorescent labels. Once again, the residual fluorescence signals due to carmine are very small.

OTHER EMBODIMENTS

While this disclosure describes specific implementations, these should not be construed as limitations on the scope of the disclosure, but rather as descriptions of features in certain embodiments. Features that are described in the context of separate embodiments can also generally be implemented in combination in a single embodiment. Conversely, various features that are described in the context of a single embodiment can also be implemented in multiple embodiments separately or in any suitable sub-combination. Moreover, although features may be described above as present in certain combinations and even initially claimed as such, one or more features from a claimed combination can generally be excised from the combination, and the claimed combination may be directed to a sub-combination or variation of a sub-combination.

In addition to the embodiments expressly disclosed herein, it will be understood that various modifications to the embodiments described may be made without departing from the spirit and scope of the disclosure. Accordingly, other embodiments are within the scope of the following claims.

What is claimed is:

1. A method, comprising:
    applying a first stain composition to a biological sample, and measuring information corresponding to one or more stains of the first stain composition in the biological sample, wherein the one or more stains comprise a fluorescent counterstain;
    removing the fluorescent counterstain from the biological sample;
    applying a second stain composition to the biological sample, and measuring information corresponding to one or more stains of the second stain composition in the biological sample, wherein the one or more stains comprise a fluorescent label;
    generating a first image of the biological sample, wherein the first image corresponds to a pattern of simulated hematoxylin staining in the biological sample; and
    generating a second image of the biological sample, wherein the second image corresponds to localization of the fluorescent label in the biological sample.

2. The method of claim 1, wherein the fluorescent counterstain comprises curcumin.

3. The method of claim 1, wherein the fluorescent counterstain comprises carmine.

4. The method of claim 1, further comprising, before applying the second stain composition to the biological sample, applying a third stain composition to the biological sample, wherein the third stain composition comprises eosin.

5. The method of claim 1, further comprising, before applying the second stain composition to the biological sample, applying a third stain composition to the biological sample, wherein the third stain composition comprises indigo carmine.

6. The method of claim 4, wherein the first image corresponds to a pattern of simulated hematoxylin and eosin staining in the biological sample.

7. The method of claim 5, wherein the first image corresponds to a pattern of simulated eosin staining and simulated hematoxylin staining in the biological sample.

8. The method of claim 1, wherein removing the fluorescent counterstain comprises exposing the biological sample to an antigen retrieval agent.

9. The method of claim 4, further comprising removing the fluorescent counterstain and eosin by exposing the biological sample to an antigen retrieval agent.

10. The method of claim 5, further comprising removing the fluorescent counterstain and indigo carmine by exposing the biological sample to an antigen retrieval agent.

11. The method of claim 1, wherein the first stain composition comprises a fixative agent.

12. The method of claim 11, wherein the fixative agent comprises potassium aluminum sulfate dodecahydrate.

13. The method of claim 1, comprising generating the first image prior to applying the second stain composition to the biological sample.

14. The method of claim 1, comprising generating the first image based on the information corresponding to the one or more stains of the first stain composition in the biological sample.

15. The method of claim 13, further comprising determining the second stain composition based on the first image.

16. The method of claim 13, further comprising identifying a set of one or more locations in the biological sample in which to identify a target analyte based on the first image.

17. The method of claim 13, further comprising annotating the first image before applying the second stain composition to the biological sample.

18. The method of claim 13, further comprising annotating the first image during application of the second stain composition to the biological sample.

19. The method of claim 1, wherein the second stain composition comprises multiple different fluorescent labels each linked to a probe for a different target within the biological sample.

20. The method of claim 19, further comprising generating one or more additional images of the biological sample, each of the additional images corresponding to localization of one or more of the different fluorescent labels in the biological sample.

21. The method of claim 1, wherein applying the second stain composition to the sample comprises:
    (a) applying a first binding agent to the biological sample, wherein the first binding agent comprises a probe that binds to a target in the sample and a nucleic acid sequence linked to the probe; and
    (b) applying a first labeling agent to the biological sample, wherein the first labeling agent comprises a nucleic acid sequence and the fluorescent label linked to the nucleic acid sequence, and wherein the first labeling agent hybridizes selectively to the first binding agent.

22. The method of claim 21, further comprising measuring fluorescence emission information from the fluorescent label.

23. The method of claim 22, further comprising in step (a) applying a plurality of different first binding agents to the biological sample, wherein each different first binding agent comprises a probe that binds to a different target in the sample and a different nucleic acid sequence linked to the probe.

24. The method of claim 23, further comprising, after measuring the fluorescence emission information, removing the first labeling agent from the biological sample.

25. The method of claim 24, further comprising applying a second labeling agent to the biological sample, wherein the second labeling agent comprises a nucleic acid sequence and a second fluorescent label linked to the nucleic acid sequence, wherein the second fluorescent label is different from the fluorescent label of the first labeling agent, and wherein the second labeling agent hybridizes selectively to a second binding agent in the sample different from the first binding agent.

26. The method of claim 25, further comprising measuring fluorescence emission information from the second fluorescent label.

27. The method of claim 1, wherein generating the first image comprises measuring fluorescence emission information for the fluorescent counterstain in the biological sample.

28. The method of claim 6, wherein generating the first image comprises measuring fluorescence emission information for the fluorescent counterstain in the biological sample and measuring absorption of incident radiation by eosin in the biological sample.

29. The method of claim 7, wherein generating the first image comprises measuring fluorescence emission information for the fluorescent counterstain in the biological sample and measuring absorption of incident radiation by indigo carmine in the biological sample.

30. A method, comprising:
- applying a first stain composition to a biological sample that comprises at least one of curcumin and carmine lake;
- applying a second stain composition to the biological sample that comprises at least one of eosin and indigo carmine;
- measuring image information corresponding to the first and second stain compositions in the biological sample;
- exposing the biological sample to at least one antigen retrieval agent to remove the at least one of curcumin and carmine lake and the at least one of eosin and indigo carmine from the biological sample;
- applying a third stain composition to the biological sample, wherein the third stain composition comprises a fluorescent label;
- measuring image information corresponding to the third stain composition in the biological sample; and
- generating a first image based on the image information corresponding to the first and second stain compositions in the biological sample that represents a hematoxylin and eosin staining distribution in the biological sample.

* * * * *